United States Patent
Ishida et al.

(10) Patent No.: US 8,357,836 B2
(45) Date of Patent: Jan. 22, 2013

(54) AGROBACTERIUM-MEDIATED METHOD FOR PRODUCING TRANSFORMED MAIZE OR RICE

(75) Inventors: Yuji Ishida, Iwata (JP); Yukoh Hiei, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 12/935,525

(22) PCT Filed: Mar. 24, 2009

(86) PCT No.: PCT/JP2009/055791
§ 371 (c)(1),
(2), (4) Date: Sep. 29, 2010

(87) PCT Pub. No.: WO2009/122962
PCT Pub. Date: Aug. 10, 2009

(65) Prior Publication Data
US 2011/0030101 A1 Feb. 3, 2011

(30) Foreign Application Priority Data
Mar. 31, 2008 (JP) ................................. 2008-094049

(51) Int. Cl.
*A01H 1/00* (2006.01)

(52) U.S. Cl. .................. 800/294; 800/320.1; 435/430.1; 435/424

(58) Field of Classification Search .................. 800/294, 800/320.1; 435/424, 430.1
See application file for complete search history.

(56) References Cited

U.S. PATENT DOCUMENTS

| | | | |
|---|---|---|---|
| 6,603,061 B1 * | 8/2003 | Armstrong et al. ........... | 800/294 |
| 7,902,426 B1 | 3/2011 | Hiei et al. | |
| 2004/0210961 A1 * | 10/2004 | Palys ........................... | 800/278 |
| 2005/0097641 A1 | 5/2005 | Wolters et al. | |
| 2007/0136898 A1 | 6/2007 | Ishida | |
| 2007/0163007 A1 | 7/2007 | Ishida | |
| 2010/0132066 A1 | 5/2010 | Ishida et al. | |
| 2011/0030100 A1 | 2/2011 | Hiei et al. | |

FOREIGN PATENT DOCUMENTS

| | | |
|---|---|---|
| EP | 1 964 919 A1 | 9/2008 |
| WO | WO 98/54961 A2 | 12/1988 |
| WO | WO 02/12520 A1 | 2/2002 |
| WO | WO 02/12521 A1 | 2/2002 |
| WO | WO 03/010319 A2 | 2/2003 |
| WO | WO 2005/017152 A1 | 2/2005 |
| WO | WO 2005/017169 A1 | 2/2005 |
| WO | WO 2007/069643 A | 6/2007 |
| WO | WO 2008/105509 A1 | 9/2008 |
| WO | WO 2008/119136 A | 10/2008 |

OTHER PUBLICATIONS

Cheng et al. Invited Review: Factors influencing Agrobacterium-mediated transformation of *monocotyledonous* species. In Vitro Cell. Dev. Biol.—Plant 40:31-45, 2004.*
Gao et al. Efficient genetic transformation fo Sorghum using a visual screening marker. Genome 48: 321-333 (2005).*
Abstract of KR 2005 0028255 dated Mar. 22, 2005.
de Vetten et al., "A transformation method for obtaining marker-free plants of a cross-pollinating and vegetatively propagated crop," Nature Biotechnology (Apr. 2003) vol. 21, pp. 439-442.
European Search Report issued May 23, 2011, in European Patent Application No. 09727983.0.
Hu et al., "Agrobacterium-mediated transformed transgenic triploid bermudagrass (*Cynodon dactylon x C. transvaalensis* ) plants are highly resistant to the glufonsinate herbicide Liberty," Plant Cell. Tissue and Organ Culture (2005) vol. 83, pp. 13-19.
Jia et al., "Direct creation of marker-free tobacco plants from agroinfiltrated leaf discs," Plant Cell Rep (2007) vol. 26, pp. 1961-1965.
Kumar et al., "In vitro plant regeneration and genetic transformation of Dichanthium annulatum," DNA and Cell Biology (2005) vol. 24, No. 11, pp. 670-679.
Li et al., "Production of selectable marker-free transgenic tobacco plants usine a non-selection approach: chimerism or escape, transgene inheritance, and efficiency," Plant Cell Rep (2009) vol. 28, pp. 373-386.
Rommens, "All-native DNA transformation: a new approach to plant genetic engineering," TRENDS in Plant Science (Sep. 2004) vol. 9, No. 9, pp. 457-464.
Weeks et al., "Development of an in planta method for transformation of alfalfa (*Medicago sativa* )," Transgenic Res (2008) vol. 17, pp. 587-597.
Bevan et al., "A chimaeric antibiotic resistance gene as a selectable marker for plant cell transformation," Nature (Jul. 1983) vol. 304, pp. 184-187.
Chan et al., "Agrobacterium-mediated production of transgenic rice plants expressing a chimeric alpha-amylase promoter/beta-glucuronidase gene," Plant Molecular Biology (1993) vol. 22, pp. 491-506.
Cheng et al., "Genetic transformation of wheat mediated by *Agrobacterium tumefaciens*," Plant Physiol. (1997) vol. 115, pp. 971-980.
Chu, "The N6 medium and its applications to another culture of cereal crops," In Proc. Symp. Plant Tissue Culture. Peking: Science Press, pp. 43-50 (1978).
Comai et al., "Expression in plants of a mutant aroA gene from *Salmonella typhimurium* confers tolerance to glyphosphate," Nature (Oct. 1985) vol. 317, pp. 741-744.

(Continued)

*Primary Examiner* — June Hwu
(74) *Attorney, Agent, or Firm* — Birch, Stewart, Kolasch & Birch, LLP (57) ABSTRACT

An *Agrobacterium*-mediated method for producing transformed maize or rice, culturing an *Agrobacterium*-inoculated immature embryo with a coculture medium and a regeneration step for culturing the immature embryo with a regeneration medium either without callus growth or after callus growth culture to regenerate whole transformed maize or rice. The method further includes a transformation enhancement and the method does not include any selection step based on the properties of a nucleic acid to be introduced by *Agrobacterium* in any step from coculture to regeneration.

7 Claims, 3 Drawing Sheets

OTHER PUBLICATIONS

De Block et al,. "Engineering herbicide resistance in plants by expression of a detoxifying enzyme," The EMBO Journal (1987) vol. 6, No. 9, pp. 2513-2518.

De Cleene et al., "The Host Range of Crown Gall," The Botanical Review (Oct.-Dec. 1976) vol. 42, No. 4, pp. 389-466.

Deji et al., "Genomic organization and transcriptional regulation of maize ZmRR1 and ZmRR2 encoding cytokinin-inducible response regulators," Biochimica et Biophysica Acta (2000) vol. 1492, pp. 216-220.

Ebinuma et al., "Selection of marker-free transgenic plants using the isopentyl transferase gene," Proc. Natl. Acad. Sci. USA (Mar. 1997), vol. 94, pp. 2117-2121.

Elliott et al., "Agrobacterium-mediated transformation of sugarcane using GFP as a screenable marker," Aust. J. Plant Physiol. (1998) vol. 25, pp. 739-743.

Erikson et al., "The dsdA gene from *Escherichia coli* provides a novel selectable marker for plant transformation," Plant Molecular Biology (2005) vol. 57, pp. 425-433.

Frame et al., "*Agrobacterium tumefaciens*-mediated transformation of maize embryos using a standard binary vector system," Plant Physiology (May 2002) vol. 129, pp. 13-22.

Frame et al., "Improved Agrobacterium-mediated transformation of three maize inbred lines using MS salts," Plant Cell Rep. (2006) vol. 25, pp. 1024-1034.

Gleave et al., "Selectable marker-free transgenic plants without sexual crossing: transient expression of cre recombinase and use of conditional lethal dominant gene," Plant Molecular Biology (1999) vol. 40, pp. 223-235.

Gould et al., "Transformation of Zea mays L using *Agrobacterium tumefaciens* and the shoot apex," Plant Physiol. (1991) vol. 95, pp. 426-434.

Grimsley et al., "Agrobacterium-mediated delivery of infectious maize steak virus into maize plants," Nature (Jan. 1987) vol. 325, pp. 177-179.

Grimsley et al., "DNA transfer from Agrobacterium to Zea mays or Brassica by agroinfection is dependent on bacterial virulence functions," Mol. Gen. Genet (1989) vol. 217, pp. 309-316.

Grimsley et al., "Meristematic tissues of maize plants are most susceptible to agroinfection with maize steak virus," Bio/Technology (Feb. 1988) vol. 6, pp. 185-189.

Haldrup et al., "The xylose isomerase gene from *Thermoanaerobacterium thermosulfurogenes* allows effective selection of transgenic plant cells using D-xylose as the selection agent," Plant Molecular Biology (1998) vol. 37, pp. 287-296.

Hiei et al., "Efficient transformation of rice (*Oryza sativa* L.) mediated by Agrobacterium and sequence analysis of the boundaries of the T-DNA," The Plant Journal (1994) vol. 6, No. 2, pp. 271-282.

Hiei et al., "Improved frequency of transformation in rice and maize by treatment of immature embryos with centrifugation and heat prior to infection with *Agrobacterium tumefaciens*," Plant Cell Tiss Organ Cult (2006), vol. 87, pp. 233-243.

International Search Report issued Apr. 21, 2009, in PCT International Application No. PCT/JP2009/055791, 2 pp.

Ishida et al., "High efficiency transformation of maize (*Zea mays* L.) mediated by *Agrobacterium tumefaciens*," Nature Biotechnology (Jun. 1996) vol. 14, pp. 745-750.

Ishida et al., "Improved protocol for transformation of maize (*Zea mays* L.) mediated by *Agrobacterium tumefaciens*," Plant Biotechnology (2003) vol. 20, No. 1, pp. 57-66.

Joersbo et al., "Analysis of mannose selection used for transformation of sugar beet," Molecular Breeding (1998) vol. 4, pp. 111-117.

Komari et al., "Vectors carrying two separate T-DNAs for co-transformation of higher plants mediated by *Agrobacterium tumefaciens* and segregation of transformants free from selection markers," The Plant Journal (1996) vol. 10, No. 1, pp. 165-174.

Komari, "Transformation of callus cultures of nine plant species mediated by *Agrobacterium*," Plant Science (1989) vol. 60, pp. 223-229.

Kuiper et al., "Assessment of the food safety issues related to genetically modified foods," The Plant Journal (2001) vol. 27, No. 6, pp. 503-528.

Mooney et al., "*Agrobacterium tumefaciens*-gene transfer into wheat tissues," Plant Cell. Tissue and Organ Culture (1991) vol. 25, pp. 209-218.

Negrotto et al., "The use of phosphomannose-isomerase as a selectable marker to recover transgenic-maize plants (*Zea mays* L.) via *Agrobacterium* transformation," Plant Cell Reports (2000) vol. 19, pp. 798-803.

Nomura et al., "The evolution of C4 plants: acquisition of cis-regulatory sequences in the promoter of C4-type pyruvate, orthophosphate dikinase gene," The Plant Journal (2000) vol. 22, No. 3, pp. 211-221.

Nomura et al., "The promoter of rbcS in a C3 plant (rice) directs organ-specific, light-dependent expression in a C4 plant (maize), but does not confer bundle sheath cell-specific expression," Plant Molecular Biology (2000) vol. 44, pp. 99-106.

Potrykus et al., "Genetic Engineering of Crop Plants," Agricultural Biotechnology, Marcel Deker Inc., New York pp. 119-159 (1998).

Potrykus, "Gene Transfer to Cereals: An Assessment," Bio/Technology (Jun. 1990) vol. 8, pp. 535-542.

Raineri et al., "*Agrobacterium*-mediated transformation of rice (*Oryza sativa* L.)," Bio/Technology (Jan. 1990) vol. 8, pp. 33-38.

Sambrook et al., "Analysis of Genomic DNA by Southern Hybridization," Molecular Cloning: A Laboratory Manual, 2nd ed., Cold Spring Harbor Laboratory Press. Cold Spring Harbor, New York, pp. 9.31-9.62 (1989).

Takematsu, Josozai Kenkyo Soran (Overview of Herbicide Research) Hakuyu-sha, Tokyo, pp. 79-153, (1982).

Taniguchi et al., "The promoter of the maize C4 pyruvate, orthophosphate dikinase gene directs cell- and tissue-specific transcription in transgenic maize plants," Plant Cell Physiol. (2000) vol. 41, No. 1, pp. 42-48.

Tingay et al., "*Agrobacterium tumefaciens*-mediated barley transformation," The Plant Journal (1997) vol. 11, No. 6, pp. 1369-1376.

Trifonova et al., "*Agrobacterium*-mediated transgene delivery and integration into barley under a range of in vitro culture conditions," Plant Science (2001), vol. 161 pp. 871-880.

Waldron et al., "Resistance to hygromycin B," Plant Molecular Biology (1985) vol. 5, pp. 103-108.

Zhang et al., "Cre/lox-mediated marker gene excision in transgenic maize (Zea mays L.) plants," Theor Appl Genet (2003) vol. 107, pp. 1157-1168.

Zhao et al., "*Agrobacterium*-mediated sorghum transformation," Plant Molecular Biology (2000) vol. 44, pp. 789-798.

Zhao et al., "High throughput genetic transformation mediated by *Agrobacterium tumefaciens* in maize," Molecular Breeding (2001) vol. 8, pp. 323-333.

Zhu et al., "Green fluorescent protein as a visual selection marker for papaya (*Carica papaya* L.) transformation," Plant Cell Rep (2004) vol. 22, pp. 660-667.

Bent, "Arabidopsis in planta transformation. Uses, mechanisms, and prospects for transformation of other species," Plant Physiology (Dec. 2000) vol. 124, pp. 1540-1547.

* cited by examiner

AGROBACTERIUM-MEDIATED METHOD FOR PRODUCING TRANSFORMED MAIZE OR RICE

TECHNICAL FIELD

The present application claims priority to Japanese Patent Application No. 2008-094049 filed on Mar. 31, 2008.

The present invention relates to a novel *Agrobacterium*-mediated method for producing a transformed plant.

BACKGROUND ART

Methods previously known for transformation of monocotyledons such as maize and rice, which are major grain crops, include electroporation, particle gun transformation, etc. However, these physical gene transfer methods have problems in that genes are introduced as multiple copies or are not inserted in an intact state, and the resulting transformed plants may often develop malformations and sterility.

*Agrobacterium*-mediated gene transfer is universally used as a transformation method for dicotyledons. Although it has been understood that hosts of *Agrobacterium* are limited only to dicotyledons and *Agrobacterium* has no ability to infect monocotyledons (De Cleene and De Ley 1976), some attempts have been made to transform monocotyledons through *Agrobacterium*-mediated method.

Grimsley et al. have reported that when maize streak virus DNA was inserted into T-DNA of *Agrobacterium* and inoculated into maize growing points, infection with maize streak virus was confirmed. Since such infection symptoms are not observed simply when the maize streak virus DNA alone is inoculated, Grimsley et al. have recognized that the above observation indicates the ability of *Agrobacterium* to introduce DNA into maize (Grimsley et al. 1987). However, this result is not indicative of T-DNA integration into nuclei, because a virus will multiply even when not integrated into a nuclear genome. Grimsley et al. have further demonstrated that the highest infection efficiency is observed upon inoculation into a growing point in the shoot apex of maize (Grimsley et al. 1988), and that the VirC gene in plasmids of *Agrobacterium* is essential for infection (Grimsley et al. 1989).

Gould et al. injured maize growing points with a needle and then inoculated these growing points with super-virulent *Agrobacterium* EHA1 carrying the kanamycin resistance gene and the GUS gene, followed by kanamycin selection on the treated growing points to obtain a resistant plant. Upon Southern analysis to confirm whether progeny seeds of this plant have the introduced gene, they confirmed that some seeds had the transgene (Gould et al. 1991). This indicates that the whole plant obtained by kanamycin selection on *Agrobacterium*-treated growing points had both transformed and non-transformed cells (chimerism).

Mooney et al. attempted to introduce the kanamycin resistance gene into wheat embryos by using *Agrobacterium*. First, the embryos were enzymatically treated to injure their cell walls, and then inoculated with *Agrobacterium*. Among the treated calli, very few calli were grown that appeared to be resistant to kanamycin, but no whole plant was regenerated from these calli. Upon Southern analysis to confirm the presence of the kanamycin resistance gene, all the resistant calli were found to have a structural mutation in the transgene (Mooney et al. 1991).

Raineri et al. performed super-virulent *Agrobacterium* A281 (pTiBo542) treatment on 8 varieties of rice whose scutellum had been injured, and they confirmed tumorous tissue growth in 2 varieties of Nipponbare, Fujisaka 5. Further, when rice embryos were inoculated with *Agrobacterium* carrying a Ti plasmid modified to have the kanamycin resistance gene and the GUS gene wherein hormone synthesis genes in T-DNA have been removed, the growth of kanamycin-resistant calli was observed. In these resistant calli, GUS gene expression was observed, but no transformed plant was obtained. Based on these results, Raineri et al. have recognized that the *Agrobacterium* T-DNA was introduced into rice cells (Raineri et al. 1990).

As shown above, there are study reports suggesting that *Agrobacterium*-mediated gene transfer is also possible for Gramineae crops including rice, maize and wheat, but these reports failed to show persuasive results because these studies had a problem in reproducibility and were also insufficient for transgene confirmation (Potrykus 1990).

Chan et al. injured immature rice embryos, which had been cultured for 2 days in the presence of 2,4-D, and then inoculated these embryos with *Agrobacterium* carrying genes for npt II and GUS in a medium containing suspension-cultured potato cells. They cultured the thus treated immature embryos on a G418-containing medium to obtain regenerated plants from the induced calli. They confirmed the location of the GUS gene in the regenerated plants and their progeny plants by Southern analysis, and reported that the presence of the transgene was observed in plants of both R0 and R1 generations (Chan et al. 1993). This result supports *Agrobacterium*-mediated transformation in rice, but the transformation efficiency was as low as 1.6%. Moreover, there was only one regenerated plant that showed normal growth, although 250 immature embryos were used for testing. Since enormous efforts are required to extract immature embryos of rice, such low transformation efficiency is not practical.

In recent years, it has been reported that stable and highly efficient transformation is also possible in monocotyledons including rice and maize when using a super-binary vector carrying a part of the virulence gene from super-virulent *Agrobacterium* (Hiei et al. 1994, Ishida et al., 1996). These reports suggest that *Agrobacterium*-mediated transformation not only allows stable and highly efficient transformation, but is also advantageous in that the resulting transformed plants have fewer mutations, and in that the introduced genes are low in copy number and are often in an intact state. Following success in rice and maize, further reports were issued for *Agrobacterium*-mediated transformation in other major grain crops, i.e., wheat (Cheng et al. 1997), barley (Tingay et al. 1997) and sorghum (Zhao et al. 2000).

In addition to the above, other attempts have been made to improve the efficiency of *Agrobacterium*-mediated maize transformation, as exemplified by selection of transformed cells on N6 basal medium (Zhao et al. 2001); addition of $AgNO_3$ and carbenicillin to culture medium (Zhao et al. 2001, Ishida et al. 2003); and addition of cysteine to coculture medium (Frame et al. 2002). As shown above, modifications to the medium composition or selection marker genes also result in improved efficiency of *Agrobacterium*-mediated transformation in rice and maize.

However, in almost all the methods previously reported for *Agrobacterium*-mediated transformation in rice or maize, a transformed plant is obtained from a callus derived from an *Agrobacterium*-inoculated scutellum or immature embryo through the steps of allowing a transformed callus to selectively grow on a medium containing a herbicide component or an antibiotic, and placing the resulting transformed cell clump onto a regeneration medium to induce regeneration (Deji et al., 2000; Negrotto et al., 2000; Nomura et al., 2000a; Nomura et al., 2000b; Taniguchi et al., 2000; Frame et al., 2002; Zhang et al., 2003; Frame et al. 2006).

In plant transformation methods, selection of transformed cells is imperative for production of transformed plants, and it has been believed that plant transformation cannot succeed in the absence of this step (Potrykus et al., 1998; Erikson et al., 2005; Joersbo et al., 2001). In most cases, selection of transformed cells is accomplished as follows: a plant material is introduced with a gene resistant to a drug that inhibits proliferation of non-transformed cells, and then cultured with a medium containing this drug, whereby only transformed cells expressing the drug resistance gene integrated into the plant cell genome are allowed to selectively proliferate.

Among genes used for selection of transformed cells (selection marker genes), the most commonly used are genes conferring resistance to herbicides or antibiotics (Kuiper et al. 2001). Genes conferring resistance to herbicides include the bar gene and the EPSP gene (De Block et al., 1987; Comai et al., 1985), while genes conferring resistance to antibiotics include the NPTII gene and the HPT gene (Bevan et al., 1983; Waldron et al., 1985), each of which is often used as a selection marker gene for plant transformation. Moreover, recent reports have shown that genes conferring the ability to metabolize a specific sugar(s), e.g., the PMI gene and the Xy1A gene (Joersbo et al., 1998; Haldrup et al., 1998) are also effective as selection marker genes. As selection marker genes based on the mechanism for allowing transformed cells to selectively proliferate, many genes have been reported in addition to those mentioned above. Moreover, in transformation methods using these genes, a selection step of allowing transformed cells to selectively proliferate is regarded as essential.

In the case of in planta transformation in which flower bud tissue is transformed by immersion under reduced pressure, transformed seeds are obtained without any selection step (Bent, 2000). However, to obtain desired transformed seeds from a mixture containing many non-transformed seeds, a selection step using an antibiotic resistance gene or the like is required.

There are reports of a method which involves introducing the GFP gene and visually screening transformed sites by detection of cells exhibiting fluorescence under ultraviolet irradiation to obtain a transformed plant (Elliott et al., 1998; Zhu et al., 2004). This method does not select transformed cells from a mixture containing non-transformed cells based on differences in their growth, but it requires a selection step for distinguishing and isolating transformed cells from non-transformed cells based on the presence or absence of GFP gene expression.

Techniques reported for removing a selection marker gene from a transformed plant include a co-transformation system (Komari et al., 1996), a MAT vector system (Ebinuma et al., 1997) and a CreLox system (Gleave et al., 1999; Zhang et al., 2003). When using these systems, it is possible to obtain a transformed plant free from a selection marker gene. However, in the course of the production of a selection marker-free transformed plant, it is necessary to perform a step of distinguishing and isolating transformed cells from non-transformed cells by using a conventionally used drug resistance gene or plant hormone synthesis gene, etc.

As shown above, the methods previously used for plant transformation must involve a selection step for isolating transformed cells from non-transformed cells. This selection step requires a selection marker gene used for selection purposes, in addition to a gene of interest (GOI gene), as shown above. By means of a reaction caused by the action of a protein or enzyme produced upon expression of this selection marker gene (e.g., herbicide resistance, antibiotic resistance or fluorescence emission), a very few transformed cells among many non-transformed cells can be distinguished and grown to obtain a transformed plant. However, such a selection marker gene is no longer required for a produced transformed plant, and many common consumers are insecure about the use of transformed plants because when selection marker genes remain in the transformed plants, the risk of spreading herbicide resistance genes or antibiotic resistance genes to normal non-recombinant plants via transformants is not negligible. Moreover, many types of selection marker genes are reported, but they have limited use depending on the species of plants, which will cause a problem when multiple genes are introduced separately. Further, although some techniques are reported for removing a selection marker gene from a transformant, these techniques require enormous efforts, including use of a longer culture period than that of standard transformation and/or isolation of selection marker-free plants among progeny plants.

As described above, many reports have been issued for production of transformed plants, but there is no report of a method for obtaining a transformant without requiring any selection step for isolating a transformed cell, tissue, organ or whole plant from non-transformed cells, tissues, organs or whole plants. Namely, it has been impossible so far to obtain a transformed plant by introducing only a GOI (Gene of Interest) gene.

Patent Publication No. 1: WO98/54961
Patent Publication No. 2: WO02/12520
Patent Publication No. 3: WO02/12521
Patent Publication No. 4: WO2005/017169
Patent Publication No. 5: WO2005/017152
Patent Publication No. 6: WO2007/069643
Non-patent Publication No. 1: De Cleene, M. and De Ley, J. (1976) The host range of crown gall. Bot. Rev. 42:389-466.
Non-patent Publication No. 2: Grimsley, N., Horn, T., Davis, J. W. and Horn, B. (1987) *Agrobacterium*-mediated delivery of infectious maize streak virus into maize plants. Nature 325:177-179.
Non-patent Publication No. 3: Grimsley, N. H., Ramos, C., Hein, T. and Horn, B. (1988) Meristematic tissues of maize plants are most susceptible to Agroinfection with maize streak virus. Bio/tecnology 6:185-189.
Non-patent Publication No. 4: Grimsley, N., Horn, B., Ramos, C., Kado, C. and Rogowsky, P. (1989) DNA transfer from *Agrobacterium* to *Zea mays* or *Brassica* by agroinfection is dependent on bacterial virulence functions. Mol. Gen. Genet. 217:309-316.
Non-patent Publication No. 5: Gould, J., Devey, M., Hasegawa, O., Ulian, E. C., Peterson, G. and Smith, R. H. (1991) Transformation of *Zea mays* L. using *Agrobacterium tumefaciens* and shoot apex. Plant Physiol. 95:426-434.
Non-patent Publication No. 6: Mooney, P. A., Goodwin, P. B., Dennis, E. S, and Llewellyn, D. J. (1991) *Agrobacterium tumefaciens*-gene transfer into wheat tissues. Plant Cell, Tissues and Organ Culture 25:209-218.
Non-patent Publication No. 7: Raineri, D. M., Bottino, P., Gordon, M. P. and Nester, E. W. (1990) *Agrobacterium*-mediated transformation of rice (*Oryza sativa* L.). Bio/technology 8:33-38.
Non-patent Publication No. 8: Potrycus, I (1990) Gene transfer to cereals: an assessment. Bio/technology 8:535-542.
Non-patent Publication No. 9: Chan, M-T., Chang, H-H., Ho, S-L., Tong, W-F. and Yu, S-M. (1993) *Agrobacterium*-mediated production of transgenic rice plants expressing a chimeric α-amylase promoter/β-glucuronidase gene. Plant Mol. Biol. 22:491-506.

Non-patent Publication No. 10: Hiei, Y., Ohta, S., Komari, T. and Kumashiro, T. (1994) Efficient transformation of rice (*Oryza sativa* L.) mediated by *Agrobacterium* and sequence analysis of the boundaries of the T-DNA. The Plant Journal 6:271-282.

Non-patent Publication No. 11: Ishida, Y., Saito, H., Ohta, S., Hiei, Y., Komari, T. and Kumashiro, T. (1996) High efficiency transformation of maize (*Zea mays* L.) mediated by *Agrobacterium tumefaciens*. Nature Biotechnology 14:745-750.

Non-patent Publication No. 12: Cheng, M., Fry, J. E., Pang, S., Zhou, H., Hironaka, C. M., Duncan, D. R., Conner, T. W., Wan, Y. (1997) Genetic transformation of wheat mediated by *Agrobacterium tumefaciens*. Plant Physiol. 115: 971-980.

Non-patent Publication No. 13: Tingay, S., McElroy, D., Kalla, R., Fieg, S., Wang, M., Thornton, S., Brettell, R. (1997) *Agrobacterium tumefaciens*-mediated barley transformation. Plant J. 11: 1369-1376.

Non-patent Publication No. 14: Zhao, Z.-Y., Cai, T., Tagliani, L., Miller, M., Wang, N., Peng, H., Rudert, M., Schoeder, S., Hondred, D., Seltzer, J., Pierce, D. (2000) *Agrobacterium*-mediated sorghum transformation. Plant Mol. Biol. 44: 789-798.

Non-patent Publication No. 15: Deji, A., Sakakibara, H., Ishida, Y., Yamada, S., Komari, T., Kubo, T., Sugiyama, T. (2000) Genomic organization and transcriptional regulation of maize ZmRR1 and ZmRR2 encoding cytokinin-inducible response regulators. Biochim. et Biophys. Acta 1492: 216-220.

Non-patent Publication No. 16: Negrotto, D., Jolley, M., Beer, S., Wenck, A. R., Hansen, G. (2000) The use of phosphomannose-isomerase as a selection marker to recover transgenic maize plants (*Zea mays* L.) via *Agrobacterium* transformation. Plant Cell Reports 19: 798-803.

Non-patent Publication No. 17: Nomura, M., Sentoku, N., Nishimura, A., Lin, J-H., Honda, C., Taniguchi, M., Ishida, Y., Ohta, S., Komari, T., Miyao-Tokumori, M., Kono-Murakami, Y., Tajima, S., Ku, M. S. B., Matsuoka, M. (2000a) The evolution of C4 plants: acquisition of cis-regulatory sequences in the promoter of C4-type pyruvate, orthophosphate dikinase gene. Plant J. 22: 211-221.

Non-patent Publication No. 18: Nomura, M., Katayama, K., Nishimura, A., Ishida, Y., Ohta, S., Komari, T., Miyao-Tokutomi, M., Tajima, S., Matsuoka, M. (2000b) The promoter of rbcS in a C3 plant (rice) directs organ-specific, light-dependent expression in a C4 plant (maize), but does not confer bundle sheath cell-specific expression. Plant Mol. Biol. 44: 99-106.

Non-patent Publication No. 19: Taniguchi, M., Izawa, K., Ku, M. S. B., Lin, J-H., Saito, H., Ishida, Y., Ohta, S., Komari, T., Matsuoka, M., Sugiyama, T. (2000) The promoter for the maize $C_4$ pyruvate, orthophosphate dikinase gene directs cell- and tissue-specific transcription in transgenic maize plants. Plant Cell Physiol. 41: 42-48.

Non-patent Publication No. 20: Zhao, Z.-Y., Gu, W., Cai, T., Tagliani, L., Hondred, D., Bond, D., Schroeder, S., Rudert, M., Pierce, D. (2001) High throughput genetic transformation mediated by *Agrobacterium tumefaciens* in maize. Mol. Breed. 8: 323-333.

Non-patent Publication No. 21: Frame, B. R., Shou, H., Chikwamba, R. K., Zhang, Z., Xiang, C., Fonger, T. M., Pegg, S. E. K., Li, B., Nettleton, D. S., Pei, D., Wang, K. (2002) *Agrobacterium tumefaciens*-mediated transformation of maize embryos using a standard binary vector system. Plant Physiol. 129: 13-22.

Non-patent Publication No. 22: Ishida, Y., Saito, H., Hiei, Y., Komari, T. (2003) Improved protocol for transformation of maize (*Zea mays* L.) mediated by *Agrobacterium tumefaciens*. Plant Biotechnology 20:57-66.

Non-patent Publication No. 23: Zhang, W., Subbarao, S., Addae, P., Shen, A., Armstrong, C., Peschke, V., Gilbertson, L. (2003) Cre/lox-mediated marker gene excision in transgenic maize (*Zea mays* L.) plants. Theor. Appl. Genet. 107: 1157-1168.

Non-patent Publication No. 24: Frame, B. R., McMurray, J. M., Fonger, T. M., Main, M. L., Taylor, K. W., Torney, F. J., Paz, M. M., Wang, K. (2006) Improved *Agrobacterium*-mediated transformation of three maize inbred lines using MS salts. Plant Cell Rep. 25: 1024-1034.

Non-patent Publication No. 25: Hiei, Y., Ishida, Y., Kasaoka, K. & Komari, T. Improved frequency of transformation in rice and maize by treatment of immature embryos with centrifugation and heat prior to infection with *Agrobacterium tumefaciens*. Plant Cell, Tissue and Organ Culture 87, 233-243 (2006).

Non-patent Publication No. 26: Hiei, Y. & Komari, T. Improved protocols for transformation of indica rice mediated by *Agrobacterium tumefaciens*. Plant Cell, Tissue and Organ Culture 85, 271-283 (2006).

Non-patent Publication No. 27: Komari, T. Transformation of callus cultures of nine plant species mediated by *Agrobacterium*. Plant Sci. 60, 223-229 (1989).

Non-patent Publication No. 28: Bent, A. F. (2000) *Arabidopsis* in planta transformation. Uses, mechanisms, and prospects for transformation of other species. Plant Physiol., 124:1540-1547.

Non-patent Publication No. 29: Bevan, M. W., Flavell, R. B., Chilton, M.-D. (1983) A chimaeric antibiotic resistance gene as a selectable marker for plants cell transformation. Nature, 304:184-187.

Non-patent Publication No. 30: Comai, L., Facciotti, D., Hiatt, W. R., Thompson, G., Rose, R. E., Stalker, D. M. (1985) Expression in plants of a mutant aroA gene from *Salmonella typhimurium* confers tolerance to glyphosate. Nature, 317:741-744.

Non-patent Publication No. 31: De Block, M., Botterman, J., Vandewiele, M., Dockx, J., Thoen, C., Gosselé, V., Movva, N. R., Thompson, C., Van Montagu, M., Leemans, J. (1987) Engineering herbicide resistance in plants by expression of a detoxifying enzyme. EMBO J., 6:2513-2518.

Non-patent Publication No. 32: Ebinuma, H., Sugita, K., Matsunaga, E., Yamakado, M. (1997) Selection of marker-free transgenic plants using the isopentenyl transferase gene as a selectable marker. Proc. Natl. Acad. Sci. U.S.A., 94:2117-2121.

Non-patent Publication No. 33: Elliott, A. R., Campbell, J. A., Brettell R. I. S., Grof, C. P. L. (1998) *Agrobacterium*-mediated transformation of sugarcane using GFP as a screenable marker. Aust. J. Plant Physiol., 25:739-743.

Non-patent Publication No. 34: Erikson, O. S., Hertzberg, M., Näsholm, T. (2005) The dsdA gene from *Escherichia coli* provides a novel selectable marker for plant transformation. Plant Mol. Biol., 57:425-433.

Non-patent Publication No. 35: Gleave, A. P., Mitra, D. S., Mudge, S. R., Morris, B. A. M. (1999) Selectable marker-free transgenic plants without sexual crossing: transient expression of cre recombinase and use of a conditional lethal dominant gene. Plant. Mol. Biol., 40:223-235.

Non-patent Publication No. 36: Haldrup, A., Petersen, S. G., Okkels, F. T. (1998) The xylose isomerase gene from Thermoanaerobacterium thermosulfurogenes allows effective selection of transgenic plant cells using D-xylose as the selection agent. Plant Mol. Biol., 37:287-296.

Non-patent Publication No. 37: Joersbo, M., Donaldson, I., Kreiberg, J., Petersen, S. G., Brunstedt, J., Okkels, F. T. (1998) Analysis of mannose selection used for transformation of sugar beet. Mol. Breed., 4:111-117.

Non-patent Publication No. 38: Komari, T., Hiei, Y., Saito, Y., Murai, N., Kumashiro, T. (1996) Vectors carrying two separate T-DNAs for co-transformation of higher plants mediated by *Agrobacterium tumefaciens* and segregation of transformants free from selection markers. The Plant Journal, 10:165-174.

Non-patent Publication No. 39: Kuiper, H. A., Meter, G. A., Noteborn, H. P. J. M., Kok, E. J. (2001) Assessment of the food safety issues related to genetically modified food. The Plant Journal, 27:503-528.

Non-patent Publication No. 40: Potrykus, I., Bilang, R., Fütterer J., Sautter, C., Schrott, M. (1998) Genetic engineering of crop plants. Agricultural Biotechnology, Marcel Deker Inc., New York. 119-159.

Non-patent Publication No. 41: Tetsuo Takematsu (1982), Josozai Kenkyu Soran (Overview of Herbicide Research), Hakuyu-sha, Tokyo, 79-154 (in Japanese).

Non-patent Publication No. 42: Waldron, C., Murphy, E. B., Roberts, J. L., Gustafson, G. D., Armour, S. L., Malcolm, S. K. (1985) Resistance to hygromycin B: A new marker for plant transformation studies. Plant Mol. Biol., 5:102-108.

Non-patent Publication No. 43: Zhu, Y. J., Asbayani, R., Moore, P. H. (2004) Green fluorescent protein as a visual selection marker for papaya (*Carica papaya* L.) transformation. Plant Cell Rep., 22:660-667.

Non-patent Publication No. 44: Chu, C.-C. (1978) The N6 medium and its applications to anther culture of cereal crops. In Proc. Symp. Plant Tissue Culture. Peking: Science Press, pp. 43-50.

Non-patent Publication No. 45: Sambrook, J., Fritsch, E. F., Maniatis, T. (1989) Molecular Cloning: A Laboratory Manual, 2nd ed., Cold Spring Harbor Laboratory Press, Cold Spring Harbor, N.Y.

DISCLOSURE OF THE INVENTION

Problems to be Solved by the Invention

Conventional methods for *Agrobacterium*-mediated gene transfer into monocotyledons must involve a selection step for isolating a transformed cell, tissue, organ or whole plant through introduction of a selection marker gene. The present invention aims to develop and provide a method by which a transformed plant can be obtained without such a selection step.

Means for Solving the Problems

As a result of extensive and intensive efforts made to solve the problems stated above, the inventors of the present invention have found that when monocotyledons are treated to improve their transformation efficiency, transformed plants can be obtained with practical efficiency without the need to introduce any selection marker gene.

More specifically, by focusing on the fact that plant cells into which a foreign gene is integrated are generally very few in number during the process of plant transformation, the inventors of the present invention have conceived that transformed plants can be obtained without any selection step which requires a selection marker gene, if the efficiency of transformation is improved greatly enough to increase the percentage of transformed cells among non-transformed cells and this state can be maintained until regeneration of whole plants. As a result of extensive and intensive efforts, the inventors have found that appropriate transformation enhancement enables the production of transformed plants with sufficiently practical efficiency, and thus have arrived at the present invention.

The present invention includes, but is not limited to, the following embodiments as preferred ones.

Embodiment 1

An *Agrobacterium*-mediated method for producing a transformed plant, which comprises:
(i) a coculture step for culturing an *Agrobacterium*-inoculated plant material with a coculture medium; and
(ii) a regeneration step for culturing the tissue obtained in (i) with a regeneration medium, either without callus growth culture or after callus growth culture, to thereby regenerate a whole plant,
wherein 1) said method comprises transformation enhancement, and
wherein 2) said method does not comprise selection of transformed cells with a selective drug in any step from coculture to regeneration.

Embodiment 2

The method according to Embodiment 1, wherein 3) said method further does not comprise any step for culturing the cocultured tissue with a callus growth medium between the coculture step and the regeneration step.

Embodiment 3

The method according to Embodiment 1 or 2, wherein a nucleic acid to be introduced by *Agrobacterium* does not carry a resistance gene for the selective drug.

Embodiment 4

The method according to any one of Embodiments 1 to 3, wherein the transformation enhancement in 1) is intended to improve the efficiency of introducing a gene of interest into plant cells, to improve the efficiency of inducing a callus from an immature embryo, or to improve the efficiency of regeneration from a transformed callus.

Embodiment 5

The method according to any one of Embodiments 1 to 4, wherein the transformation enhancement in 1) is selected from the group consisting of:
thermal treatment;
centrifugation;
thermal treatment and centrifugation;
pressurization;
addition of silver nitrate and/or copper sulfate to the coculture medium;
inoculation with *Agrobacterium* in the presence of a powder;
addition of carbenicillin to the medium in the callus growth and/or regeneration step following the coculture step;
addition of N6 inorganic salts to the callus growth medium; and
addition of cysteine to the coculture medium.

Embodiment 6

The method according to any one of Embodiments 1 to 5, wherein said method comprises addition of a compound belonging to benzoic herbicides in the coculture step.

Embodiment 7

The method according to Embodiment 6, wherein the compound belonging to benzoic herbicides is of benzoic acid type, salicylic acid type or picolinic acid type.

Embodiment 8

The method according to Embodiment 6 or 7, wherein the compound belonging to benzoic herbicides is 3,6-dichloro-o-anisic acid or 4-amino-3,5,6-trichloropicolinic acid.

Embodiment 9

The method according to any one of Embodiments 1 to 8, wherein the plant is a monocotyledon.

Embodiment 10

The method according to any one of Embodiments 1 to 9, wherein the plant is maize or rice.

PREFERRED EMBODIMENTS OF THE INVENTION

The present invention provides an *Agrobacterium*-mediated method for producing a transformed plant. The present invention is directed to a method for *Agrobacterium*-mediated gene transfer into a plant, which is based on the finding that enhancement of transformation efficiency eliminates the need to introduce a selection marker gene. The method of the present invention is an *Agrobacterium*-mediated method for producing a transformed plant, which comprises:

(i) a coculture step for culturing an *Agrobacterium*-inoculated plant material with a coculture medium; and (ii) a regeneration step for culturing the tissue obtained in (i) with a regeneration medium, either without callus growth culture or after callus growth culture, to thereby regenerate a whole plant, wherein 1) said method comprises transformation enhancement, and wherein 2) said method does not comprise selection of transformed cells with a selective drug in any step from coculture to regeneration.

Transformation Enhancement

One of the features of the present invention lies in comprising transformation enhancement. In the method of the present invention, "transformation enhancement" refers to treatment by which the percentage of the resulting transformed plants is increased. Specific examples include, but are not limited to, those intended to improve the efficiency of introducing a gene of interest into plant cells, to improve the efficiency of inducing a callus from an immature embryo, and to improve the efficiency of regeneration from a transformed callus. Such transformation enhancement includes, but is not limited to, the following or any combination thereof:

thermal treatment (see WO98/54961),
centrifugation (see WO02/12520),
thermal treatment and centrifugation (see WO02/12521),
pressurization (see WO2005/017169),
addition of silver nitrate and/or copper sulfate to the coculture medium (see Zhao et al. 2001, Ishida et al. 2003 for AgNO$_3$; WO2005/017152 for CuSO$_4$),
inoculation with *Agrobacterium* in the presence of a powder (see WO2007/069643),
addition of carbenicillin to the medium in the callus growth and/or regeneration step following the coculture step (see Zhao et al. 2001, Ishida et al. 2003),
addition of N6 inorganic salts (Chu 1978) to the callus growth medium (Zhao et al. 2001), and
addition of cysteine to the coculture medium (Frame et al. 2002).

Among them, thermal treatment, centrifugation, thermal treatment and centrifugation, pressurization, and addition of a powder are each intended to improve the efficiency of gene transfer, while addition of silver nitrate, copper sulfate or carbenicillin has the effect of improving the efficiency of callus induction. Alternatively, addition of copper sulfate to the regeneration medium is intended to improve the efficiency of regeneration.

Without being limited thereto, thermal treatment may be accomplished, for example, as described in WO98/54961. By way of example, a plant material is treated at 33° C. to 60° C., preferably at 37° C. to 52° C., for 5 seconds to 24 hours, preferably for 1 minute to 24 hours before being contacted with *Agrobacterium*.

Centrifugation may be accomplished, for example, as described in WO02/12520. By way of example, a plant material is treated at a centrifugal acceleration of 100 G to 250,000 G, preferably, 500 G to 200,000 G, more preferably 1000 G to 150,000 G, for 1 second to 4 hours, more preferably for 1 second to 2 hours before being contacted with *Agrobacterium*.

Thermal treatment and centrifugation may be accomplished, for example, as described in WO02/12521. Conditions used for thermal treatment and centrifugation may be, for example, the same as those mentioned above.

Pressurization may be accomplished, for example, as described in WO2005/017169. Pressurization is performed preferably within the range of, but not limited to, 1.7 to 10 atm, more preferably 2.4 to 8 atm.

Addition of silver nitrate and/or copper sulfate to the coculture medium can be found, for example, in Zhao et al. 2001, Ishida et al. 2003, and WO2005/017152. Silver nitrate and/or copper sulfate may be added to the coculture medium at a concentration of 1 to 50 µM, preferably 1 to 10 µM.

Inoculation with *Agrobacterium* in the presence of a powder may be accomplished, for example, as described in WO2007/069643. More specifically, an *Agrobacterium* suspension and a powder may be mixed together and inoculated into a plant material, or alternatively, a plant and a powder may be mixed together and then inoculated with *Agrobacterium*, by way of example. Any powder may be used for this purpose, including porous powders, glass wool or activated charcoal, preferably porous ceramics, glass wool or activated charcoal, more preferably hydroxyapatite, silica gel or glass wool.

Addition of N6 inorganic salts to the callus growth medium (Zhao et al. 2001) is accomplished by addition of N6 inorganic salts (Chu 1978) to the callus growth medium.

In the case of addition of cysteine to the coculture medium, cysteine may be added to the coculture medium at 10 mg/l to 1 g/l, preferably 50 mg/l to 750 mg/l, more preferably 100 mg/l to 500 mg/l.

Addition of carbenicillin to the medium in the callus growth and/or regeneration step following the coculture step may be accomplished as described in Zhao et al. 2001 or Ishida et al. 2003. Carbenicillin may be added at a concentration of 50 mg/l to 500 mg/l, preferably 100 mg/l to 300 mg/l to a medium for callus growth and/or during the regeneration step. It should be noted that carbenicillin, which is an antibiotic, has little toxicity to plants and can be used for the purpose of preventing microbial growth in the medium.

Those skilled in the art would be able to perform these treatments at appropriate timings under appropriate conditions. Moreover, for enhancement of transformation efficiency, these treatments are more preferably combined as appropriate. For example, in the case of maize, it is desirable to combine two or more treatments selected from thermal treatment and centrifugation, powder treatment, addition of $AgNO_3$ and/or $CuSO_4$ to the coculture medium, and addition of carbenicillin as an antibiotic in the callus growth medium and/or in the regeneration medium. In the case of rice, it is preferable to use thermal treatment and/or centrifugation, most preferably in combination with addition of carbenicillin as an antibiotic in the callus growth medium and/or in the regeneration medium.

Thus, preferred transformation enhancement is thermal treatment, centrifugation, thermal treatment and centrifugation, pressurization, addition of $AgNO_3$ and/or $CuSO_4$ to the coculture medium, or inoculation with *Agrobacterium* in the presence of a powder, addition of carbenicillin as an antibiotic in the callus growth medium and/or in the regeneration medium, or any combination thereof.

The inventors of the present invention have succeeded in sufficiently increasing the number of transformed whole plants among finally obtained regenerated whole plants upon these treatments, and have found that a sufficient number of transformed whole plants can be obtained without selection of transformed cells, thereby establishing a practicable method for selection-free transformation.

These transformed whole plants may be easily obtained by confirming the presence or absence of a transgene by PCR or other procedures. Likewise, their progeny plants may be easily obtained by confirming the phenotype of the transgene.

Selection of Transformed Cells

The present invention is characterized in that it does not comprise selection of transformed cells based on the properties of a nucleic acid to be introduced by *Agrobacterium* in any step from coculture to regeneration required for plant transformation.

As an example of selection of transformed cells based on the properties of a nucleic acid to be introduced by *Agrobacterium*, selection of transformed cells with a selective drug and a resistance gene for the selective drug can be presented.

"Selection of transformed cells with a selective drug and a resistance gene for the selective drug" is intended to mean that cells are cultured in a medium supplemented with a drug for selection of a transformed plant to select transformed cells based on the presence or absence of resistance to the selective drug, in any step from coculture to regeneration required for plant transformation. The present invention is completely free from such a step.

Examples of selective drugs used in conventional techniques are antibiotics and/or herbicides. Antibiotics conventionally used include those having toxicity to plants, such as hygromycin, kanamycin or blasticidin S, and herbicides conventionally used include phosphinothricin, bialaphos or glyphosate, etc.

For this step, DNA inserted into T-DNA in *Agrobacterium* needs to comprise not only a gene to be expressed in a plant, but also a resistance gene for a selective drug. Such a resistance gene for a selective drug is known in the art. For example, when a regeneration medium containing hygromycin as a selective drug is used for regeneration, the hygromycin resistance gene should be introduced from *Agrobacterium* into the plant.

Since the present invention requires no drug selection step, a nucleic acid to be introduced by *Agrobacterium* does not need to carry a resistance gene for a selective drug, i.e., a selection marker gene. Thus, without being limited thereto, in a preferred embodiment, the present invention is free from such a nucleic acid.

In another conventional method, a transformed plant may also be selected based on "auxotrophic selection" (e.g., "sugar requirement") of plant cells.

In the case of sugar requirement, sugars assimilable by plant cells include sucrose, glucose and so on, but it is known that mannose cannot be assimilated. Thus, when cultured with a medium containing mannose as the only carbon source, plant tissues will die because there is no assimilable sugar. Selection based on sugar requirement relies on this principle. When a transformed plant is selected based on sugar requirement, a gene enabling the assimilation of sugars that are generally not assimilable by plant cells should be introduced from *Agrobacterium* into the plant tissue. Such a gene is known in the art and, for example, the PMI gene, the xylose isomerase gene or the like may be used for this purpose. In the present invention, a nucleic acid to be introduced does not need to comprise such a gene.

In another conventional method, an easily detectable gene may be introduced as a screening indicator to select a transformed plant based on the presence or absence of expression of this gene. Examples of such a gene serving as a screening indicator include the GFP gene, etc. In the present invention, a nucleic acid to be introduced does not need to comprise such a gene.

In the method of the present invention, the term "selection marker gene" is intended to mean an additional gene that is introduced into a plant together with a gene of interest (GOI gene) to be transformed, for the purpose of selecting transformed cells from among many non-transformed cells. Examples of such a selection marker gene include, but are not limited to, herbicide resistance genes, antibiotic resistance genes, fluorescent genes and so on.

Method for Producing Transformed Plant

An *Agrobacterium*-mediated method for producing a transformed plant generally involves all or part of Steps I to V shown below.

I. Plant material preparation step
II. *Agrobacterium* preparation and inoculation step
III. Coculture step
IV. Callus growth step
V. Regeneration step I. Plant Material Preparation Step Plants targeted by the present invention are those to which *Agrobacterium*-mediated transformation is applicable. Preferred are monocotyledons. Monocotyledons used in the method of the present invention are preferably Gramineae plants including, but not limited to, rice, maize, barley, wheat, sorghum and so on. The most preferred plant used in the method of the present invention is rice or maize.

In the method of the present invention, the term "plant material" is intended to encompass all embodiments of such a plant to be used for *Agrobacterium*-mediated plant transformation, including a cell, a leaf, a root, a stem, a bud, a flower (including a stamen, a pistil, etc.), a fruit, a seed, a germinated seed or a plant tissue of any other site, a growing point, an explant, an immature embryo, a callus or an embryoid-like tissue (hereinafter collectively referred to as "callus or the like" or simply "callus"), or a perfect whole plant.

A preferred form of the plant material used in the method of the present invention is an immature embryo or a callus, most preferably an immature embryo. The expressions "plant cell," "plant tissue" and "perfect whole plant" used herein have the same meanings as commonly used in the art. As used herein, the term "immature embryo" is intended to mean the embryo and scutellum of an immature seed under maturation after pollination. The stage (maturation phase) of the immature embryo used in the method of the present invention is not limited in any way, and it may be collected at any stage after pollination. It is most preferably at a post-pollination stage of 2 days or more. It is preferable to use the scutellum of an immature embryo capable of inducing a callus having the ability to grow and regenerate a normal whole plant by the method described later after the transformation described later. Moreover, such an immature embryo is preferably an immature embryo of an inbred line, F1 between inbred lines, F1 between an inbred line and an open-pollinated variety, or a commercially available F1 variety. As used herein, the term "callus" is intended to mean an undifferentiated cell clump under uncontrolled growth. To obtain a callus, differentiated cells of a plant tissue may be cultured in a medium containing a plant growth regulator such as auxin (e.g., 2,4-D) or cytokinin (referred to as a dedifferentiation medium). This treatment for obtaining a callus is referred to as dedifferentiation treatment, and this process is referred to as dedifferentiation process.

In this step, if necessary, a plant tissue, an immature embryo or the like is excised from a whole plant, a seed or the like to prepare a plant material preferred for use in transformation. Preparation of a plant material may be accomplished in any known manner. If desired, a plant material may be cultured before being infected with *Agrobacterium*.

II. *Agrobacterium* Preparation and Inoculation Step

The plant material used in the present invention is inoculated with *Agrobacterium*. The term "inoculation" or "inoculated" used herein is intended to mean that *Agrobacterium* is contacted with a plant material, and various techniques for *Agrobacterium* inoculation are known in the art. Examples of such techniques include those in which a plant material is added to a suspension of *Agrobacterium* suspended in a liquid medium, those in which an *Agrobacterium* suspension is directly added dropwise to a plant material on a coculture medium, those in which an *Agrobacterium* suspension is injected into a plant material, and those in which a plant material is immersed in an *Agrobacterium* suspension and incubated under reduced pressure. However, the *Agrobacterium*-inoculated plant material used in the present invention is not limited to those inoculated with *Agrobacterium* by these techniques.

In this *Agrobacterium* inoculation step, to improve the *Agrobacterium*-mediated transformation efficiency, for example, various additives (e.g., acetosyringone, surfactants, porous ceramics) may be incorporated into an *Agrobacterium* suspension.

*Agrobacterium* that can be used in the present invention may be any known species of *Agrobacterium*, preferably *Agrobacterium tumefaciens* or *Agrobacterium rhizogenes*. In a preferred embodiment of the present invention, examples of *Agrobacterium* include, but are not limited to, LBA4404, EHA101 and AGL1, C58C1 and others.

A soil bacterium *Agrobacterium* (*Agrobacterium tumefaciens*) has been known to cause crown gall disease in many dicotyledons since a long time ago, and in 1970s, it was found that its Ti plasmid was involved in pathogenicity, and that T-DNA, a part of the Ti plasmid, was integrated into the plant genome. Subsequently, it has been shown that T-DNA contains genes involved in synthesis of hormones (cytokinin and auxin) required to induce cancer, and these genes are expressed in plants although they are bacterial genes. A group of genes located in the virulence region (vir region) on the Ti plasmid are required for excision of T-DNA and its transfer to plants, and border sequences flanking T-DNA are required for excision of T-DNA. *Agrobacterium rhizogenes*, another species of *Agrobacterium*, has a similar system based on Ri plasmid (e.g., FIGS. 3 and 4 of JP 2000-342256 A).

Since T-DNA is integrated into the plant genome upon *Agrobacterium* infection, it was expected that a desired gene would also be integrated into the plant genome when inserted onto T-DNA. However, it was difficult to insert a gene onto T-DNA on Ti plasmid by standard genetic engineering techniques, because Ti plasmid is as large as 190 kb or more. For this reason, there was developed a method for inserting a foreign gene onto T-DNA.

First, disarmed strains in which hormone synthesis genes have been removed from T-DNA of tumor-inducing Ti plasmid were prepared, including LBA4404 (see Hoekema, A., et al., (1983), Nature, Vol. 303, p. 179-180), C58C1 (pGV3850), GV3Ti11SE, etc. With the use of these strains, two methods were developed, one for introducing a desired gene into T-DNA of *Agrobacterium* Ti plasmid and another for introducing T-DNA carrying a desired gene into *Agrobacterium*. The first method is called the intermediate vector method, in which an intermediate vector easy to genetically manipulate enough to insert a desired gene thereinto and capable of replicating in *E. coli* is introduced into the T-DNA region of a disarmed Ti plasmid in *Agrobacterium* by homologous recombination via triparental mating.

The second method is called the binary vector method, which is based on the finding that the vir region is required for integration of T-DNA into plants but needs not be located on the same plasmid to exert its functions. This vir region contains virA, virB, virC, virD, virE and virG (Dictionary of Plant Biotechnology, published by Enterprise (1989)), and the vir region is intended to mean a region containing all of these virA, virB, virC, virD, virE and virG. The term "binary vector" refers to a vector carrying T-DNA integrated into a small plasmid replicable in both *Agrobacterium* and *E. coli*, and this binary vector is introduced into *Agrobacterium* having a disarmed Ti plasmid before use.

Introduction of a binary vector into *Agrobacterium* can be accomplished in any known manner, for example, by electroporation or triparental mating. Examples of a binary vector include pBIN19, pBI121, pGA482, etc., and many new binary vectors have been constructed based on these vectors and used for transformation. In the Ri plasmid system, similar vectors have been constructed and used for transformation.

*Agrobacterium* A281 is a super-virulent strain that has a wide host range and higher transformation efficiency than other strains. This characteristic is attributed to pTiBo542, i.e., the Ti plasmid of A281. Two novel systems have been developed so far with the use of pTiBo542. One of them uses strains EHA101 and EHA105, each carrying a disarmed Ti plasmid of pTiBo542, and is used for transformation of various plants as a system with high transforming ability by applying these strains to the binary vector system described above.

The other is a super-binary vector system. Details of super-binary vectors can be found, for example, in the following documents which are incorporated herein by reference:

Hiei, Y., et al., (1994), The Plant Journal, Vol. 6, p. 271-282;

Ishida, Y., et al., (1996), Nature Biotechnology, Vol. 4, p. 745-750;

Komari, T. and Kubo T., (1999), Methods of Genetic Transformation: *Agrobacterium tumefaciens*. In Vasil, I. K. (ed.) Molecular improvement of cereal crops., Kluwer Academic Publishers, Dordrecht, p. 43-82; and

WO95/06722.

Details of a super-binary vector system can be found, for example, in FIG. 4 of JP 2000-342256 A.

This system is a kind of binary vector system because it consists of a disarmed Ti plasmid having the vir region (virA, virB, virC, virD, virE and virG (each hereinafter also referred to as a "vir fragment region")) and a plasmid having T-DNA. However, it differs in that it uses a super-binary vector carrying a fragment of the vir region substantially free from at least one of the vir fragment regions (preferably a fragment including at least virB or virG, more preferably a fragment including virB and virG) in the plasmid having T-DNA, i.e., a binary vector. It should be noted that homologous recombination via triparental mating can be used as a convenient technique to introduce the T-DNA region carrying a desired gene into *Agrobacterium* carrying a super-binary vector.

In the method of the present invention, any species of *Agrobacterium* may be used as a host, and preferred for use is *Agrobacterium tumefaciens* (e.g., *Agrobacterium tumefaciens* LBA4404 (see Hoekema, A., et al., (1983), Nature, Vol. 303, p. 179-180) and EHA101 as mentioned above).

According to the method of the present invention, the benefit of the present invention can be obtained by using any gene transfer system as long as it relies on the expression of the genes in the virulence (vir) region in *Agrobacterium*.

For example, the benefit of the present invention can be obtained by using any vector system, including intermediate vectors, binary vectors, super-virulent binary vectors and super-binary vectors as described above, with super-virulent binary vectors and super-binary vectors being preferred because of improved transformation efficiency. (In particular, super-binary vectors are preferred for use when a target plant is maize). The same benefit can also be obtained by using different vector systems modified from the above vectors (e.g., by excising a part or all of the vir region in *Agrobacterium* and additionally integrating it into a plasmid, or by excising a part or all of the vir region and introducing it into *Agrobacterium* as a part of a new plasmid).

A desired gene to be introduced into plants can be inserted in a standard manner into a restriction enzyme site in the T-DNA region of the above plasmid. In the case of a large plasmid having many restriction enzyme sites, desired DNA may not be easily introduced into the T-DNA region by standard subcloning techniques. In such a case, desired DNA can be introduced by homologous recombination in cells of *Agrobacterium* via triparental mating. The size of a gene to be introduced is preferably, but not limited to, about 100 bp to 200 kbp.

Likewise, introduction of a plasmid into *Agrobacterium* (e.g., *Agrobacterium tumefaciens*) can be accomplished in a conventional manner, for example, by triparental mating as described above, electroporation, electroinjection, chemical treatment with PEG, etc.

A gene to be introduced into plants is basically located between the border sequences flanking T-DNA, as in the case of conventional techniques. However, only one border sequence may exist because the plasmid is circular, or alternatively, three or more border sequences may exist when multiple genes are to be located at different sites. The gene may also be located on the Ti or Ri plasmid or on another plasmid in *Agrobacterium*. Alternatively, it may also be located on multiple types of plasmids.

Inoculation of a plant material with *Agrobacterium* may be accomplished, for example, by simply establishing contact between the plant material and *Agrobacterium*. Inoculation may be accomplished by either standard inoculation or drop inoculation.

Standard inoculation is a technique in which a plant material is mixed with an *Agrobacterium* suspension (inoculum) to ensure immersion of the plant material in the suspension, and the immersed plant material is collected and placed onto a medium to effect coculture for inoculation. For example, it may be accomplished by preparing an *Agrobacterium* suspension at a cell density of about $10^6$ to $10^{11}$ cfu/ml, immersing a plant material in this suspension for about 3 to 10 minutes, and then coculturing the plant material on a solid medium for several days. Drop inoculation is a technique in which an *Agrobacterium* suspension is added dropwise onto a plant material placed on a medium, and after the suspension added dropwise is dried, the plant material is transferred to another site on the same medium or placed onto another medium to effect coculture for inoculation.

III. Coculture Step

In this step, plant cells inoculated with *Agrobacterium* as described above are cultured together with the *Agrobacterium* with a medium containing an auxin member to thereby ensure DNA introduction from the *Agrobacterium* into the plant cells. Preferably, a plant material is cocultured with *Agrobacterium* during or after infection of the plant material with *Agrobacterium* and before removal of *Agrobacterium*.

The medium used in this step is referred to herein as "coculture medium." For coculture, any known medium may be used, including LS-AS medium, nN6-AS medium, as well as N6S3-AS medium, 2N6-AS medium (see Hiei, Y., et al., (1994), The Plant Journal, Vol. 6, p. 271-282) and so on.

In the present invention, the coculture medium is preferably supplemented with an auxin member(s). Since auxin members generally have the ability to induce dedifferentiation in plant materials, almost every plant material is partially or fully turned into a dedifferentiated tissue (callus) during this step. Examples of auxin members include 3,6-dichloro-o-anisic acid (dicamba), 4-amino-3,5,6-trichloropicolinic acid (picloram), 2,4-dichlorophenoxyacetic acid (2,4-D), 2,4,5-trichlorophenoxyacetic acid (2,4,5-T) and/or triiodobenzoic acid (TIBA). In a preferred embodiment of the present invention, the coculture medium is free from any auxin member other than dicamba, picloram, 2,4-D and 2,4,5-T.

The total amount of auxin members (e.g., dicamba, picloram, 2,4-D, 2,4,5-T) in the coculture medium is preferably, but not limited to, 0.1 to 5.0 mg/l, more preferably 0.5 to 3.0 mg/l, even more preferably 1.0 to 2.0 mg/l, and most preferably 1.5 mg/l.

In a case where a plant material is from maize, the inventors of the present invention have found that transformation efficiency is further improved enough to produce a transformed plant without the need to introduce a selection marker gene, particularly when a substance with auxin activity belonging to benzoic herbicides among auxin members, is added to the coculture medium.

Based on their skeletal structure, benzoic herbicides are classified into (i) benzoic acid type, (ii) salicylic acid type, (iii) picolinic acid type, and (iv) terephthalic acid type (Takematsu, 1982). However, herbicides of (iv) terephthalic acid type have no auxin activity, and hence preferred herbicides are of (i) benzoic acid type, (ii) salicylic acid type or (iii) picolinic acid type, more preferably of either (ii) salicylic acid type or (iii) picolinic acid type. Even more preferred is dicamba (3,6-dichloro-o-anisic acid) or picloram (4-amino-3,5,6-trichloropicolinic acid). Thus, in the case of maize, the coculture medium is most preferably supplemented with a substance with auxin activity belonging to benzoic herbicides.

Alternatively, in a case where a plant material is from rice, the coculture medium is preferably supplemented with 2,4-dichlorophenoxyacetic acid (2,4-D).

The term "culture" in this step is intended to mean that a plant material is placed on a solidified coculture medium or in a liquid coculture medium and is allowed to grow at an appropriate temperature under appropriate light/dark conditions for an appropriate period. The coculture medium may be solidified by addition of any solidifying agent known in the art, including agarose. The culture temperature in this step may be selected as appropriate, and is preferably 20° C. to 35° C., more preferably 25° C. Moreover, culture in this step is preferably accomplished in the dark, but is not limited thereto. The culture period in this step may also be selected as appropriate, and is preferably 1 to 10 days, more preferably 7 days.

IV. Callus Growth Step

In *Agrobacterium*-mediated plant transformation methods, a callus growth step has generally been regarded as a necessary step.

It is possible to obtain a "cell clump containing a population of transformed cells" when the cocultured material is transferred onto a callus growth medium to induce callus growth. The term "callus growth medium" refers to a medium containing plant hormones and nutrients suitable for division and proliferation of cells in a dedifferentiated state. In standard transformation tests, it is also used as a "selective medium" by being supplemented with a drug (selection pressure), which inhibits the proliferation of non-transformed cells, to thereby ensure selective proliferation of transformed cells. Thus, in this callus growth step, the plant material after the above coculture step is cultured with a medium containing an auxin member to select a transformant based on the presence or absence of gene transfer. The medium used in this step is referred to herein as "selective medium" and contains a selective drug or the like for selection based on the presence or absence of gene transfer.

This step is repeated for several rounds in the conventional methods while varying the composition of medium components. For example, in the selection step repeated for several rounds, the selective drug concentration may be elevated at each round to ensure a higher reliability of drug selection, so that the possibility of obtaining a transformed whole plant can be increased. This selection step is preferably repeated for at least 2 rounds, more preferably 3 rounds. When repeated for several rounds, this step requires a period of about 10 days to 3 weeks for each round, and the total period required for several rounds of selection is about 5 to 10 weeks. Thus, this step is the most time-consuming step in *Agrobacterium*-mediated plant transformation.

In conventional *Agrobacterium*-mediated plant transformation methods, this step has been regarded as an essential step. However, the inventors of the present invention have found, ahead of others, that "transformation enhancement" ensures successful transformation without the need to select transformed cells with a selective drug in any step from coculture to regeneration, including during the callus growth step, and thus have arrived at the present invention. For this reason, in the present invention, this step can preferably be eliminated. Namely, the present invention does not comprise any step for culturing the cocultured tissue with a callus growth medium between the coculture step and the regeneration step. This allows a further improvement in manipulation efficiency and time saving in the transformation process, and hence the inventors have found that a transformed plant can be obtained more efficiently. Particularly in the case of maize, Examples 1-4 and 6-7 described herein later demonstrate successful cases of plant transformation without requiring any callus growth step.

Alternatively, the callus growth step may be performed without adding a selective drug to the callus growth medium. In this case, callus growth will occur but "selection" of transformants will not be performed.

V. Regeneration Step

This step involves regeneration of the resulting cell clump and growth of the regenerated plant to obtain a perfect whole plant, if desired. Regeneration of a perfect whole plant from the resulting transformed cells may be accomplished in any known manner (e.g., Hiei, Y., et al., (1994), The Plant Journal, Vol. 6, p. 271-282; and Ishida, Y., et al., (1996), Nature Biotechnology, Vol. 14, p. 745-750).

This step is essential both in conventional methods and in the present invention. It has been believed that selection of transformants with a selective drug is also essential in the regeneration step. For selection of transformed plants, the plant material after the coculture step is cultured with a regeneration medium containing a selective drug and then tested for the presence or absence of resistance to the selective drug. However, the present invention is characterized in that it does not comprise selection of transformed cells with a selective drug in any step from coculture to regeneration required for plant transformation. Thus, the present invention does not comprise selection with a selective drug even in the regeneration step.

The medium used in this step is referred to herein as "regeneration medium," which is characterized by containing no auxin member. Examples of a medium that can be used as a regeneration medium include those based on LS inorganic salts or N6 inorganic salts, more specifically LSZ medium. However, the "regeneration medium" is free from any selective drug.

The term "regeneration" used herein is intended to mean that a fully or partially dedifferentiated plant material acquires again the properties of the original plant material or whole plant. When subjected to the regeneration step, a dedifferentiated tissue will be able to regenerate, whereby a perfect transformed whole plant can be obtained. Determination of whether regeneration has occurred or not may be readily accomplished by observation of plant morphology, for example, by determining whether a specific differentiated plant organ (e.g., stem, leaf) develops from a dedifferentiated tissue.

As used herein, the term "vigor" is intended to mean the growth vigor of a regenerated plant. The vigor of a plant may be measured by any known technique used in the art. For example, in the case of maize, scoring may be performed as follows for each transformed plant tissue after the regeneration step: transformed plant tissue showing no regeneration=0, transformed plant tissue giving a regenerated shoot whose maximum length is less than 5 mm=1, transformed plant tissue giving a regenerated shoot whose maximum length is 5 mm to less than 2 cm=2, and transformed plant tissue giving a regenerated shoot whose maximum length is 2 cm or longer=3, followed by calculating a mean value for all transformed plant tissues to thereby determine their vigor. The method of evaluation of vigor is not limited to this technique, and appropriate modifications may be made to well-known techniques, e.g., depending on the type of target to be evaluated.

The term "culture" in this step is intended to mean that a plant tissue is placed on a solidified regeneration medium or in a liquid regeneration medium and is allowed to grow at an appropriate temperature under appropriate light/dark conditions for an appropriate period. The regeneration medium may be solidified, for example, with agar or the like as shown above. The culture temperature in this step may be selected as appropriate, and is preferably 20° C. to 35° C., more preferably 25° C. Moreover, culture in this step is preferably accomplished in the light for 16 to 24 hours a day, but is not limited thereto. The culture period in this step may also be selected as appropriate, and is preferably 7 to 21 days, more preferably 14 days.

After this step, a perfect transformed whole plant can be easily obtained in a manner known in the art. The presence or absence of the transgene is confirmed for each of the resulting regenerated plants to specify a transformed whole plant. Without being limited thereto, PCR or Southern analysis may be preferably used for this purpose. Moreover, isolation may be easily accomplished by confirming the phenotype of the transgene.

Advantages of the Invention

In the methods for monocotyledon transformation, the present invention ensures stable and efficient transformation in a desired plant without the need to introduce a plant selection marker gene.

BRIEF DESCRIPTION OF THE DRAWINGS

From the regenerated whole plants obtained without selection after transformation with *Agrobacterium* LBA4404 (pSB134), genomic DNAs were extracted and digested with a restriction enzyme HindIII. The digested DNAs were subjected to agarose gel electrophoresis, followed by hybridization with a GUS probe. Seed-derived Yukihikari (control) (Lane C); regenerated whole plants showing GUS-positive expression (uniform GUS expression) (Lanes 1-11); and regenerated whole plants showing a dotted pattern of GUS expression (Lanes 12-17).

Form the regenerated whole plants (maize) obtained without selection after transformation with *Agrobacterium* LBA4404 (pSB124), genomic DNAs were extracted and digested with a restriction enzyme BamHI. The digested DNAs were subjected to agarose gel electrophoresis, followed by hybridization with a GUS probe. Seed-derived A188 (control) (Lane C); and regenerated whole plants showing GUS-positive expression (uniform GUS expression) (Lanes 1-13).

From the regenerated T0 whole plants (maize) obtained without selection after transformation with *Agrobacterium* LBA4404 (pSB124) and their T1 progeny obtained by crossing with pollen of non-transformed A188 plant, genomic DNAs were extracted and digested with a restriction enzyme BamHI. The digested DNAs were subjected to agarose gel electrophoresis, followed by hybridization with a GUS probe. Whole plant (T0) of line No. 195 (Lane 1); progeny (T1) of line No. 195 showing GUS-positive expression (Lanes 2-6); and GUS-negative progeny (T1) of line No. 195 (Lane 7). Whole plant (T0) of line No. 169 (Lane 8); progeny (T1) of line No. 169 showing GUS-positive expression (Lanes 9-13); and GUS-negative progeny (T1) of line No. 169 (Lane 14).

EXAMPLES

The present invention will now be described in more detail below on the basis of the following examples, which are not intended to limit the scope of the invention.

Example 1

Gene Expression in Whole Plants Regenerated without Selection from Immature Maize Embryos Inoculated in a Standard Manner 1. Material and Method Maize (variety: A188) immature embryos (1.0 to 1.5 mm in size) at 7 to 14 days after pollination were aseptically collected and washed once with LS-inf liquid medium (Ishida et al., 1996), followed by pretreatment (thermal treatment at 46° C. for 3 minutes and centrifugation at 20,000×g for 10 minutes) to increase gene transfer efficiency for transformation enhancement (Hiei et al., 2006). In LS-inf liquid medium containing 100 µM acetosyringone, *Agrobacterium* strain LBA4404 (pSB134) (Hiei and Komari, 2006) was suspended at about $1.0 \times 10^9$ cfu/ml to prepare an inoculum.

The thermally-treated and centrifuged immature embryos were mixed with the inoculum, vortexed for 30 seconds, and then allowed to stand for 5 minutes at room temperature. The *Agrobacterium*-inoculated immature embryos were placed, with their scutella facing up, onto a coculture medium containing dicamba (3,6-dichloro-o-anisic acid) at a concentration of 1.5 mg/l in LS-AS medium (Ishida et al., 1996; solidified with 8 g/l agarose) which had been prepared to exclude 2,4-D (2,4-dichlorophenoxyacetic acid) and contain 5 µM $AgNO_3$ and 5 µM $CuSO_4$.

The immature embryos cultured in the dark at 25° C. for 7 days were placed onto LSZ medium (Ishida et al., 1996) containing 10 µM $CuSO_4$, and then cultured in the light at 25° C. for about 2 weeks. Leaves of the regenerated whole plants were partially excised and immersed in 0.1 M phosphate buffer (pH 6.8) containing 0.1% Triton X-100 and then allowed to stand at 37° C. for 1 hour. The phosphate buffer was removed and replaced by another phosphate buffer containing 1.0 mM 5-bromo-4-chloro-3-indolyl-β-D-glucuronic acid (X-gluc) and 20% methanol. After treatment at 37° C. for 24 hours, GUS gene expression was analyzed.

The conditions used in Example 1 are summarized below.
Material: immature maize embryos
Method: *Agrobacterium* inoculation in a standard manner
Transformation enhancement: thermal treatment and centrifugation, addition of $Ag^+$ and $Cu^{2+}$ ions to the medium
Auxin added to the coculture medium: dicamba
After coculture, the embryos were directly subjected to the regeneration step without passing through the callus growth step.
Vector: pSB134, a super-binary vector carrying the GUS gene and the hygromycin resistance gene (selection marker gene) and also carrying a part of the virulence gene from a super-virulent strain
Selection: no selection in any step 2. Results All of the 16 immature embryos placed on the LSZ medium were found to regenerate into whole plants. 4 to 13 leaf pieces were collected from the plant regenerated from each immature embryo and analyzed for GUS gene expression.

Leaf pieces derived from two immature embryos were all GUS-negative. In leaf pieces collected from the remaining 14 immature embryos, at least one leaf piece showed GUS gene expression in each case. Leaf pieces showing a dotted pattern of expression were observed for 5 immature embryos. Leaf pieces expressing the GUS gene in a striped pattern were observed for 6 immature embryos. There were two immature embryos giving not only leaf pieces showing a dotted pattern of expression but also leaf pieces showing a striped pattern of expression. In this case, a plant showing a striped pattern of expression is predicted to be a chimera between transformed and non-transformed cells, while a plant showing a dotted pattern of expression is predicted to have undergone gene silencing in some transformed cells. GUS-positive leaf pieces whose cut ends were uniformly stained blue were obtained from one immature embryo.

The results of this example indicate that maize plants transformed with the GUS gene were obtained under conditions where no selection step with an antibiotic or the like was performed in any step from coculture to regeneration.

Example 2

Gene Expression in Whole Plants Regenerated without Selection from Immature Maize Embryos Inoculated by the Drop Method 1. Material and Method An inoculum (1 ml) of *Agrobacterium* strain LBA4404 (pSB134) prepared in the same manner as shown in Example 1 was supplemented with about 80 mg of hydroxyapatite (Bio-Rad). Immature embryos were subjected to pretreatment (thermal treatment at 46° C. for 3 minutes and centrifugation at 20,000×g for 10 minutes) to increase gene transfer efficiency for transformation enhancement.

After the above treatment, the immature embryos (variety: A188) were placed, with their scutella facing up, onto a coculture medium containing dicamba at a concentration of 1.5 mg/l in LS-AS medium (Ishida et al., 1996; solidified with 8 g/l agarose) which had been prepared to exclude 2,4-D and contain 5 μM $AgNO_3$ and 5 μM $CuSO_4$.

After shaking with a vortex mixer to uniformly disperse hydroxyapatite in the inoculum, 5 μl of the inoculum was added dropwise to each immature embryo. After the inoculum added dropwise was dried, each immature embryo was transferred to another site on the same medium. The incubator was sealed, followed by coculture in the dark at 25° C. for 7 days. The cocultured immature embryos were cultured in the same manner as shown in Example 1 to obtain regenerated plants, and GUS gene expression was also analyzed in leaves of the regenerated plants.

The conditions used in Example 2 are summarized below.

Material: immature maize embryos

Method: *Agrobacterium* inoculation by the drop method

Transformation enhancement: powder treatment, thermal treatment and centrifugation, addition of $Ag^+$ and $Cu^{2+}$ ions to the medium Auxin added during the coculture step: dicamba After coculture, the embryos were directly subjected to the regeneration step without passing through the callus growth step.

Vector: pSB134, a super-binary vector carrying the GUS gene and the hygromycin resistance gene (selection marker gene) and also carrying a part of the virulence gene from a super-virulent strain Selection: no selection in any step 2. Results All of the 12 immature embryos placed on the LSZ medium were found to regenerate into whole plants. 3 to 17 leaf pieces were collected from the plant regenerated from each immature embryo and analyzed for GUS gene expression. Leaf pieces derived from 3 immature embryos were all GUS-negative. In leaf pieces collected from the remaining 9 immature embryos, at least one leaf piece showed GUS gene expression in each case. Leaf pieces showing a dotted pattern of expression were observed for 3 immature embryos. There were 4 immature embryos giving not only leaf pieces showing a dotted pattern of expression but also leaf pieces showing a striped pattern of expression. GUS-positive leaf pieces whose cut ends were uniformly stained blue were obtained from two immature embryos.

The results of this example indicate that maize plants transformed with the GUS gene were obtained under conditions where no selection step with an antibiotic or the like was performed in any step from coculture to regeneration.

Example 3

Effect of Auxin in Coculture Medium on Gene Expression in Whole Plants Regenerated without Selection from Immature Maize Embryos 1. Material and Method Maize (variety: A188) immature embryos (1.0 to 1.5 mm in size) at 7 to 14 days after pollination were aseptically collected and washed once with LS-inf liquid medium, followed by pretreatment (thermal treatment at 46° C. for 3 minutes) to increase gene transfer efficiency for transformation enhancement. In LS-inf liquid medium containing 100 μM acetosyringone, *Agrobacterium* strain LBA4404 (pSB124) (Komari et al., 1996) was suspended to prepare an inoculum.

The thermally-treated immature embryos were mixed with the inoculum, vortexed for 30 seconds, and then allowed to stand for 5 minutes at room temperature. The *Agrobacterium*-inoculated immature embryos (24 in total) were placed, with their scutella facing up, onto a coculture medium containing dicamba (3,6-dichloro-o-anisic acid) or picloram (4-amino-3,5,6-trichloropicolinic acid) at a concentration of 6.8 μM in LS-AS medium (Ishida et al., 1996; solidified with 8 g/l agarose) which had been prepared to exclude 2,4-D (2,4-dichlorophenoxyacetic acid) and contain 5 μM $AgNO_3$ and 5 μM $CuSO_4$.

On the other hand, LS-AS medium containing 5 μM $AgNO_3$ and 5 μM $CuSO_4$ was supplemented with 1.5 mg/l (6.8 μM) 2,4-D as an auxin member and also used for testing. 24 immature embryos were placed onto this medium.

The immature embryos cultured in the dark at 25° C. for 7 days were placed onto LSZ medium (Ishida et al., 1996) containing 10 μM $CuSO_4$, and then cultured in the light at 25° C. for about 2 weeks. Leaves of the regenerated whole plants were partially excised and immersed in 0.1 M phosphate buffer (pH 6.8) containing 0.1% Triton X-100 and then allowed to stand at 37° C. for 1 hour. The phosphate buffer was removed and replaced by another phosphate buffer containing 1.0 mM 5-bromo-4-chloro-3-indolyl-β-D-glucuronic acid (X-gluc) and 20% methanol. After treatment at 37° C. for 24 hours, GUS gene expression was analyzed.

The conditions used in Example 3 are summarized below.
Material: immature maize embryos
Method: *Agrobacterium* inoculation in a standard manner
Transformation enhancement: thermal treatment, addition of $Ag^+$ and $Cu^{2+}$ ions to the medium
Auxin added to the coculture medium: dicamba, picloram or 2,4-D
After coculture, the embryos were directly subjected to the regeneration step without passing through the callus growth step.
Vector: pSB124, a super-binary vector carrying the GUS gene but no selection marker gene and also carrying a part of the virulence gene from a super-virulent strain
Selection: no selection in any step
2. Results In the case of the immature embryos cultured with the dicamba-containing coculture medium, all of the 24 immature embryos placed on the LSZ medium were found to regenerate into whole plants. Leaves were collected from the plant regenerated from each immature embryo and analyzed for GUS gene expression. Leaf pieces derived from 13 immature embryos were all GUS-negative. In leaf pieces collected from the remaining 11 immature embryos, at least one leaf piece showed GUS gene expression in each case. The number of regenerated plants showing incomplete expression, such as a dotted pattern of expression or a striped pattern of expression, was also counted.

All of the immature embryos cultured with the picloram-containing coculture medium were found to regenerate into whole plants on the LSZ medium. Leaf pieces derived from 15 immature embryos were all GUS-negative. In leaf pieces collected from the remaining 9 immature embryos, at least one leaf piece showed GUS gene expression in each case.

Among the 24 immature embryos cocultured with the 2,4-D-containing medium, 3 immature embryos did not regenerate into plants on the LSZ medium. Among the 21 immature embryos that were found to regenerate, 4 immature embryos showed GUS gene expression in at least one leaf piece.

As shown above, the immature embryos cocultured with the medium containing particularly dicamba or picloram were found to regenerate into whole plants with higher efficiency, and also resulted in an increased percentage of regenerated plants showing expression of the transgene. The immature embryos cocultured with the 2,4-D-containing medium also showed expression of the transgene, which was slightly lower.

The results of this example indicate that maize plants transformed with the GUS gene were obtained under conditions where no selection step with an antibiotic or the like was performed in any step from coculture to regeneration. 2,4-D, dicamba and picloram are substances with auxin activity, which are among organic compounds having herbicidal activity. 2,4-D belongs to phenoxy herbicides, while dicamba and picloram differ from 2,4-D in that they belong to benzoic herbicides (Takematsu, 1982). This indicates that in the case of maize, to efficiently obtain transformed plants from immature embryos without selection, a substance belonging to benzoic herbicides is more suitable than a substance belonging to phenoxy herbicides when used as an auxin member to be incorporated into a medium for coculture of *Agrobacterium*-inoculated immature embryos.

Example 4

Effect on Gene Expression in Whole Plants Regenerated without Selection Upon Thermal Treatment and Centrifugation of Immature Maize Embryos 1. Material and Method Maize (variety: A188) immature embryos (1.0 to 1.5 mm in size) at 7 to 14 days after pollination were aseptically collected and washed once with LS-inf liquid medium, followed by pretreatment (thermal treatment at 46° C. for 3 minutes and centrifugation at 20,000×g at 4° C. for 10 minutes) to increase gene transfer efficiency for transformation enhancement. As a control, immature embryos not receiving this pretreatment were also provided for testing. In LS-inf liquid medium containing 100 μM acetosyringone, *Agrobacterium* strain LBA4404 (pSB124) was suspended to prepare an inoculum.

The thermally- and centrifugally-pretreated immature embryos and the non-pretreated control immature embryos were each mixed with the inoculum, vortexed for 30 seconds, and then allowed to stand for 5 minutes at room temperature. The *Agrobacterium*-inoculated immature embryos were placed, with their scutella facing up, onto a coculture medium containing dicamba (3,6-dichloro-o-anisic acid) at a concentration of 6.8 μM in LS-AS medium (Ishida et al., 1996; solidified with 8 g/l agarose) which had been prepared to exclude 2,4-D (2,4-dichlorophenoxyacetic acid) and contain 5 μM $AgNO_3$ and 5 μM $CuSO_4$. The pretreated and non-pretreated immature embryos were provided for testing (75 embryos each). The test was performed in duplicate.

The immature embryos cultured in the dark at 25° C. for 7 days were placed onto LSZ medium (Ishida et al., 1996) containing 10 μM $CuSO_4$, and then cultured in the light at 25° C. for about 2 weeks. Leaves of the regenerated whole plants were partially excised and immersed in 0.1 M phosphate buffer (pH 6.8) containing 0.1% Triton X-100 and then allowed to stand at 37° C. for 1 hour. The phosphate buffer was removed and replaced by another phosphate buffer containing 1.0 mM 5-bromo-4-chloro-3-indolyl-β-D-glucuronic acid (X-gluc) and 20% methanol. After treatment at 37° C. for 24 hours, GUS gene expression was analyzed.

The conditions used in Example 4 are summarized below.
Material: immature maize embryos
Method: *Agrobacterium* inoculation in a standard manner
Transformation enhancement:
(1) thermal treatment and centrifugation, addition of $Ag^+$ and $Cu^{2+}$ ions to the medium
(2) no thermal treatment and no centrifugation, although $Ag^+$ and $Cu^{2+}$ ions were added to the medium
Auxin added to the coculture medium: dicamba
After coculture, the embryos were directly subjected to the regeneration step without passing through the callus growth step.
Vector: pSB124, a super-binary vector carrying the GUS gene but no selection marker gene and also carrying a part of the virulence gene from a super-virulent strain
Selection: no selection in any step
2. Results In the first test, the thermally-treated and centrifuged 75 immature embryos were found to regenerate into 296 shoots. Among them, 5 shoots showed GUS gene expression throughout the leaf tissue. In contrast, the non-pretreated 75 immature embryos were found to regenerate into 291 shoots, although there was no shoot showing GUS gene expression throughout the leaf tissue. In the second test, the thermally-treated and centrifuged immature embryos were found to regenerate into 243 shoots, and there were four GUS-positive shoots showing GUS gene expression throughout the leaf tissue.

In the case of the immature embryos which were not pretreated by thermal treatment or centrifugation, there was only one GUS-positive shoot showing GUS gene expression throughout the leaf tissue, although 266 shoots were regenerated. These results indicate that particularly when thermal treatment and centrifugation are performed on immature embryos prior to inoculation with *Agrobacterium*, it is possible to efficiently obtain whole plants expressing the transgene throughout their tissue regenerated without selection. In the above results, the case where gene transfer was observed in only one plant would result from the effect of addition of silver nitrate and copper sulfate to the coculture medium.

Example 5

Selection-Free Transformation in Rice

1. Material and Method

Rice (variety: Yukihikari) immature seeds at 8 to 12 days after flowering were hulled and treated with 70% ethanol for several seconds and then with 1% sodium hypochlorite containing one drop of Tween20® for 5 minutes. The immature seeds were washed several times with sterilized water, and immature embryos of 1.3 to 1.8 mm in length were collected therefrom. Then, the immature embryos were centrifuged at 20,000×g for 10 minutes to increase gene transfer efficiency for transformation enhancement (Hiei et al., 2006). In AA-inf liquid medium (Hiei and Komari, 2006) containing 100 μM acetosyringone, *Agrobacterium* LBA4404 (pSB 134) (Hiei and Komari, 2006) was suspended at a concentration of about $1.0 \times 10^9$ cfu/ml to prepare an inoculum. The centrifuged immature embryos were placed, with their scutella facing up, onto nN6-As medium (Hiei et al., 2006). To the immature embryos, the inoculum was added dropwise in 5 μl volumes, followed by coculture in the dark at 25° C. for 7 days.

After coculture, each immature embryo was divided into 4 or 5 parts with a surgical knife. The divided immature embryos were placed, with their scutella facing up, onto nN6 medium (Hiei et al., 2006) containing 250 mg/l cefotaxime and 100 mg/l carbenicillin, and then cultured in the light at 30° C. for about 10 days. Sections expanded primarily by proliferation of scutellum cells were each further divided into 4 or 5 parts. At this stage, 18 to 25 sections were obtained for each immature embryo. The sections were placed, with their scutella facing up, onto nN6 medium (Hiei et al., 2006) containing 250 mg/l cefotaxime and 100 mg/l carbenicillin, and then cultured in the light at 30° C. for about 2 weeks.

After coculture, additional culture was repeated twice to induce callus growth, so that individual cells in the scutellum proliferated about 140-fold and each section was covered with calli. It should be noted that the ratio of cell proliferation was estimated from the size of each section. Among the calli formed on the sections, only one callus (0.5 to 1 mm in size) was excised from each section, placed onto N6R regeneration medium (Hiei et al., 2006) and cultured in the light at 30° C. for 2 weeks. The reason why only one callus from each section was placed onto the regeneration medium is because a whole plant originating from random and independent cells should be obtained. The shoot clump regenerated from each callus was transferred to N6F rooting medium (Hiei et al., 2006) and cultured in the light at 30° C. for about 10 days to obtain a perfect regenerated whole plant. It should be noted that the above medium is free from any selective drug, such as hygromycin, bialaphos or the like.

Leaves of the resulting whole plants were partially excised and immersed in 0.1 M phosphate buffer (pH 6.8) containing 0.1% Triton X-100® and then allowed to stand at 37° C. for 1 hour. The phosphate buffer was removed and replaced by another phosphate buffer containing 1.0 mM 5-bromo-4-chloro-3-indolyl-β-D-glucuronic acid (X-gluc) and 20% methanol. After treatment at 37° C. for 24 hours, GUS gene expression was analyzed. It should be noted that analysis of GUS gene expression was performed on at most one leaf from one whole plant for each section. Transformation efficiency was evaluated as a ratio of the number of GUS-positive whole plants (showing uniform GUS expression) relative to the number of plants analyzed for GUS gene expression.

Moreover, to confirm whether the transgene was integrated into the genomes of the regenerated whole plants, Southern blot analysis was performed in the following manner. From leaves of the regenerated whole plants, DNAs were extracted according to the method of Komari (1989) and digested in an amount of 7 μg per plant with a restriction enzyme HindIII. The digested DNAs were subjected to 0.7% agarose gel electrophoresis (1.5 V/cm, 15 hours). Southern hybridization was performed according to the method of Sambrook et al. (1989). It should be noted that the probe used was a SalI-SacI (1.9 kb) fragment of pGL2-IG (Hiei et al., 1994), which is a GUS gene fragment.

The conditions used in Example 5 are summarized below.

Material: immature rice embryos

Method: *Agrobacterium* inoculation in a standard manner

Transformation enhancement: centrifugation, addition of cefotaxime and carbenicillin to the medium Auxin added during the coculture step: 2,4-D After coculture, the embryos were subjected to the regeneration step through the callus growth step.

Vector: pSB134, a super-binary vector carrying the GUS gene and the hygromycin resistance gene (selection marker gene) and also carrying a part of the virulence gene from a super-virulent strain Selection: no selection in any step 2. Results The test was performed in duplicate (Tests 1 and 2). The results of Test 1 are shown in Table 1. In Test 1, 100 divided sections were obtained from 5 immature embryos, and 100 calli from these sections were placed onto the regeneration medium to obtain 92 whole plants. Among them, 73 whole plants were each analyzed for GUS gene expression in one leaf, indicating that 9 whole plants were GUS-positive transformants showing uniform GUS expression throughout the leaf tissue. The transformation efficiency was 12.3% per regenerated whole plant.

The results of Test 2 are shown in Table 2. In Test 2, 107 divided sections were obtained from 5 immature embryos, and 107 calli from these sections were placed onto the regeneration medium to obtain 100 whole plants. Among them, 95 whole plants were each analyzed for GUS gene expression in one leaf, indicating that 16 whole plants were transformants showing uniform GUS expression. The transformation efficiency in this case was 16.8% per regenerated whole plant. These results indicated that transformants were obtained with efficiency as high as 10% or more per regenerated whole plant, even when the selection step was eliminated.

In Test 1 and Test 2, leaf pieces of some whole plants showed GUS gene expression in a dotted pattern (Tables 1 and 2). This abnormal expression is predicted to be caused by gene silencing. It should be noted that whole plants showing such a dotted pattern of expression were not regarded as transformants.

Figure 1:
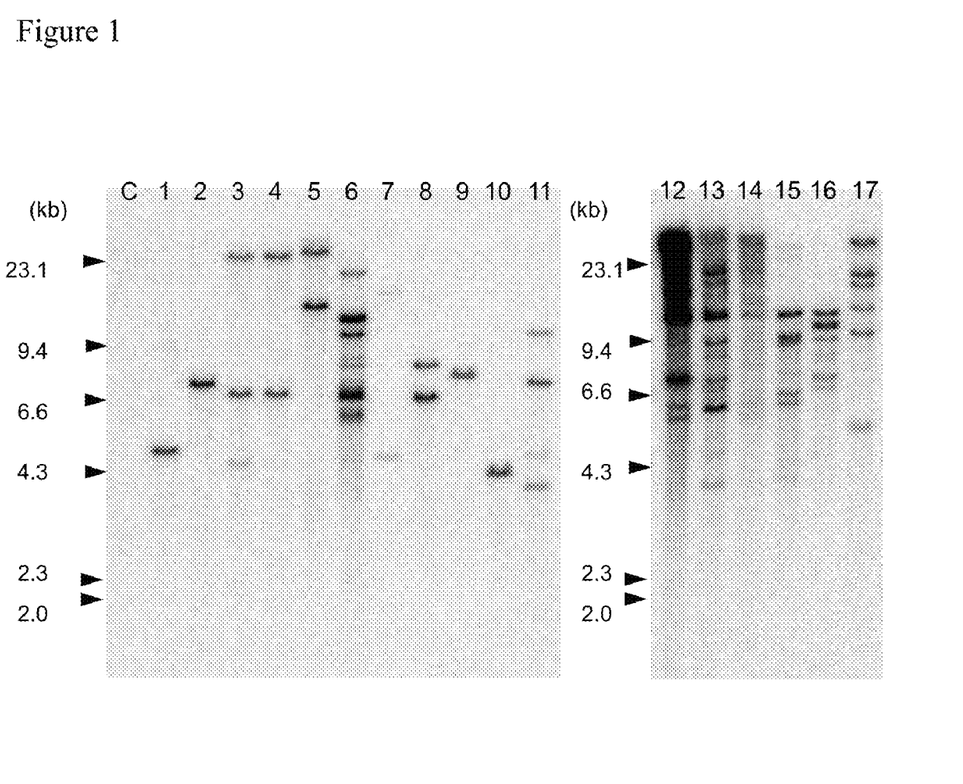
FIG. 1 shows the results of Southern blot analysis performed on regenerated whole plants of the cultivar Yukihikari obtained by selection-free transformation.

The results of Southern blot analysis are shown in FIG. 1. The regenerated whole plants positive for GUS gene expression were confirmed to have the introduced GUS gene in all of the 11 cases tested (FIG. 1). The regenerated whole plants showing GUS gene expression in a dotted pattern were also confirmed to have the GUS gene in all of the 6 cases tested, but the introduced gene in these whole plants tended to be present in a high copy number (FIG. 1). Moreover, the regenerated whole plants negative for GUS gene expression were also subjected to Southern blot analysis, but there was no band hybridizing to the GUS probe in each of the 7 whole plants tested.

In this example, scutellum cells in the gene-transferred immature embryos were allowed to proliferate, and calli were randomly extracted therefrom to obtain regenerated whole plants. 10% or more of these regenerated whole plants were found to be transformed whole plants. This indicates that 10% or more of scutellum cells in immature embryos have been transformed by *Agrobacterium* infection.

probe used was a SalI-SacI (1.9 kb) fragment of pGL2-IG (Hiei et al., 1994), which is a GUS gene fragment.

2. Results

Figure 2:
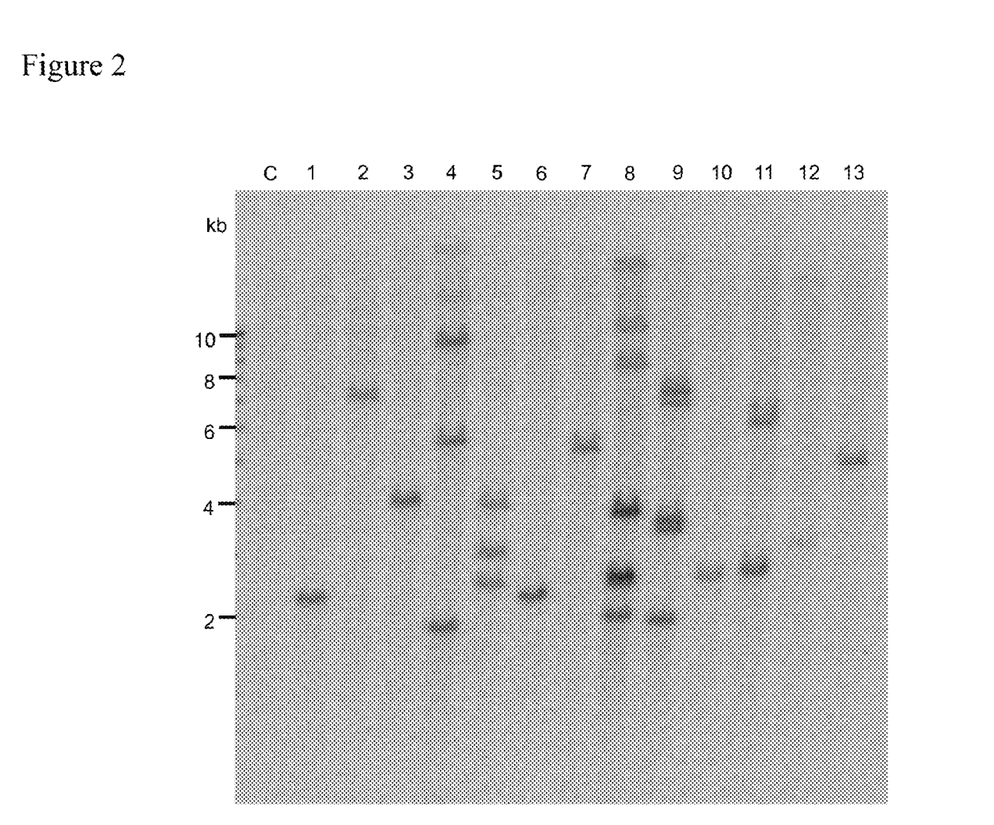
FIG. 2 shows the results of Southern blot analysis performed on regenerated whole plants of the variety A188 obtained by selection-free transformation.

Each transformant showed a band(s) hybridizing to the GUS probe. The band pattern differed from transformant to transformant, thus indicating that the transgene was randomly inserted onto the plant chromosome. In view of this fact, it was confirmed by molecular techniques that maize plants obtained by the selection-free method were transformants (FIG. 2).

TABLE 1

Production of transformants from immature rice embryos by selection-free transformation with Agrobacterium LBA4404 (pSB134) (Test 1)

| | Number of calli | | Number of whole plants | | | | |
|---|---|---|---|---|---|---|---|
| Test immature embryo | placed onto regeneration medium (= number of divided sections) | Number of calli from which regenerated whole plants were obtained | GUS expression analysis (a) | GUS-positive (uniform expression) (b) | GUS expression in a dotted pattern | GUS-negative | Transformation efficiency (b/a: %) |
| 1 | 20 | 18 | 16 | 2 | 0 | 14 | 12.5 |
| 2 | 20 | 19 | 13 | 3 | 0 | 10 | 23.1 |
| 3 | 20 | 18 | 14 | 1 | 0 | 13 | 7.1 |
| 4 | 20 | 18 | 18 | 2 | 0 | 16 | 11.1 |
| 5 | 20 | 19 | 12 | 1 | 1 | 10 | 8.3 |
| Total | 100 | 92 | 73 | 9 | 1 | 64 | 12.3 |

TABLE 2

Production of transformants from immature rice embryos by selection-free transformation with Agrobacterium LBA4404 (pSB134) (Test 2)

| | Number of calli | | Number of whole plants | | | | |
|---|---|---|---|---|---|---|---|
| Test immature embryo | placed onto regeneration medium (= number of divided sections) | Number of calli from which regenerated whole plants were obtained | GUS expression analysis (a) | GUS-positive (uniform expression) (b) | GUS expression in a dotted pattern | GUS-negative | Transformation efficiency (b/a: %) |
| 1 | 23 | 20 | 18 | 3 | 3 | 12 | 16.7 |
| 2 | 19 | 18 | 18 | 3 | 3 | 12 | 16.7 |
| 3 | 18 | 17 | 17 | 2 | 3 | 12 | 11.7 |
| 4 | 25 | 24 | 21 | 2 | 2 | 17 | 9.5 |
| 5 | 22 | 21 | 21 | 6 | 3 | 12 | 28.6 |
| Total | 107 | 100 | 95 | 16 | 14 | 65 | 16.8 |

Example 6

Southern Analysis in Transformed Maize Plants (T0) Obtained without Selection

1. Material and Method

The transformed maize plants (variety: A188) obtained in Examples 3 and 4 were cultivated in a greenhouse. From leaves of these plants, DNAs were extracted according to the method of Komari et al. (Komari et al. (1989)) and digested in an amount of 10 μg per plant with a restriction enzyme BamHI. The digested DNAs were subjected to 0.7% agarose gel electrophoresis (1.5 V/cm, 15 hours). Southern hybridization was performed according to the method of Sambrook et al. (Sambrook, J., et al., (1989) Molecular Cloning: A Laboratory Manual, 2nd ed., Cold Spring Harbor Laboratory Press, Cold Spring Harbor, N.Y.). It should be noted that the Example 7

Inheritance of Transgene to Progeny Plants in Transformed Maize Plants Obtained without Selection 1. Material and Method The transformed maize plants (variety: A188) obtained in Examples 3 and 4 were cultivated in a greenhouse. Pollen was collected from non-transformed A188 and crossed with the floss of each transformed plant to obtain progeny seeds (T1 generation).

The resulting seeds were seeded in plastic pots containing potting soil. Leaves were excised from young seedlings at 11 days after seeding, immersed in 0.1 M phosphate buffer (pH 6.8) containing 0.1% Triton X-100, and then allowed to stand at 37° C. for 1 hour. The phosphate buffer was removed and replaced by another phosphate buffer containing 1.0 mM 5-bromo-4-chloro-3-indolyl-β-D-glucuronic acid (X-gluc) and 20% methanol. After treatment at 37° C. for 24 hours, GUS gene expression was analyzed.

From leaves of the transformed plants (T0) and the above T1 plants, DNAs were extracted according to the method of Komari (1989) and digested in an amount of 10 µg per plant with a restriction enzyme BamHI. The digested DNAs were subjected to 0.7% agarose gel electrophoresis (1.5 V/cm, 15 hours). Southern hybridization was performed according to the method of Sambrook et al. (1989). It should be noted that the probe used was a SalI-SacI (1.9 kb) fragment of pGL2-IG (Hiei et al., 1994), which is a GUS gene fragment.

2. Results

Table 3 shows the results analyzed for segregation of the GUS gene in progeny plants of transformed maize plants obtained by selection-free transformation.

TABLE 3

Segregation of GUS gene in progeny plants of transformed maize plants obtained by selection-free transformation

| T0 line No. | Number of GUS-expressing plants (T1 generation) | | Ratio (positive:negative) | $\chi^2$ |
| --- | --- | --- | --- | --- |
| | Positive | Negative | | |
| 163 | 18 | 14 | 1:1 | 0.50 |
| 169 | 22 | 8 | 3:1 | 0.04 |
| 180 | 12 | 20 | 1:1 | 2.00 |
| 195 | 15 | 17 | 1:1 | 0.13 |

As shown in Table 3, all of the tested 4 lines of transformed plants showed positive and negative segregation of GUS gene expression in their progeny plants. The number of whole plants positive for GUS gene expression and the number of whole plants negative for GUS gene expression conformed to a ratio of 1:1 or 3:1 in all lines, thus indicating that the GUS gene introduced by selection-free transformation was inherited to progeny plants according to the Mendel's laws.

DNA extracted from the transformed plant (T0) of line No. 195 showed a single hybridizing band. Among T1 progeny plants of this line, DNAs extracted from five GUS-positive plants each showed a single band of the same size as in the T0 plant. In contrast, no hybridizing band was detected in DNAs extracted from GUS-negative plants.

Figure 3:
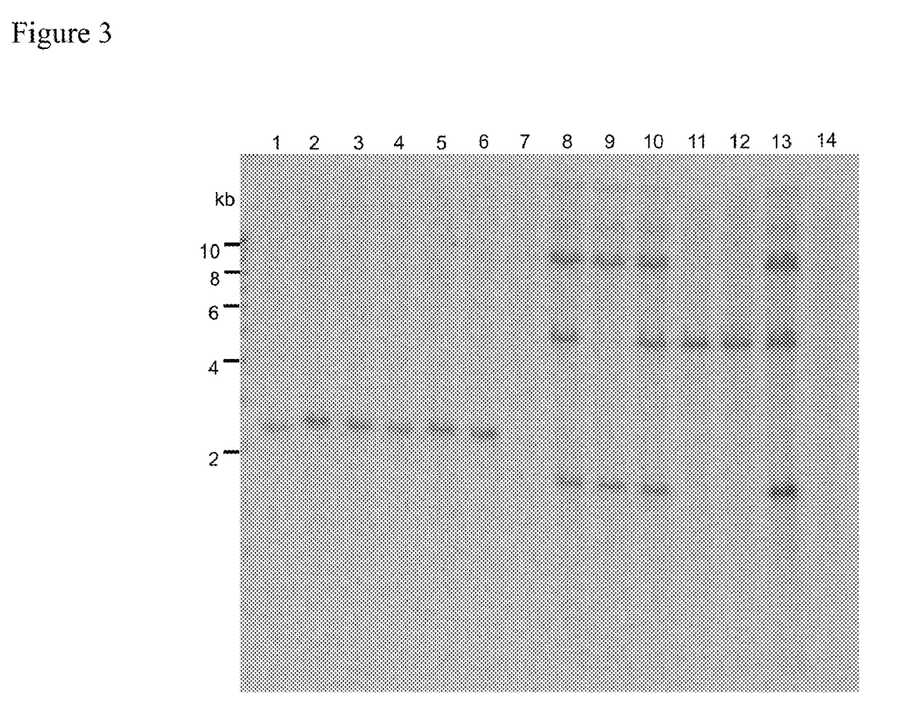
FIG. 3 shows the results of Southern blot analysis performed on regenerated whole plants (T0) of the variety A188 obtained by selection-free transformation and their T1 progeny.

DNA extracted from the transformed plant (T0) of line No. 169 showed five hybridizing bands. Among T1 progeny plants of this line, DNAs extracted from five GUS-positive plants each showed bands of the same size as in the T0 plant although the number of bands varied from 1, 4 or 5. Since GUS gene expression in T1 plants of line No. 169 showed two-factor segregation, it was predicted that 4 copies and 1 copy of the GUS gene would be located on different chromosomes, respectively. No hybridizing band was detected in DNAs extracted from GUS-negative plants (FIG. 3).

The above results indicated that the gene introduced into transformed maize plants obtained by selection-free transformation was inherited to their progeny plants according to the Mendel's laws.

The invention claimed is:

1. An *Agrobacterium*-mediated method for producing a transformed maize or rice, which comprises:
   (i) a coculture step for culturing an *Agrobacterium*-inoculated immature embryo with a coculture medium; and
   (ii) a regeneration step for culturing the immature embryo obtained in (i) with a regeneration medium, either without callus growth culture or after callus growth culture, to thereby regenerate a whole transformed maize or rice,
   wherein 1) said method comprises transformation enhancement, wherein the transformation enhancement is selected from the group consisting of:
   thermal treatment;
   centrifugation;
   thermal treatment and centrifugation;
   pressurization;
   addition of silver nitrate and/or copper sulfate to the coculture medium;
   inoculation with *Agrobacterium* in the presence of a powder;
   addition of carbenicillin to the medium in the callus growth and/or regeneration step following the coculture step;
   addition of N6 inorganic salts to the callus growth medium; and
   addition of cysteine to the coculture medium, and
   wherein 2) said method does not comprise any selection step based on the properties of a nucleic acid to be introduced by *Agrobacterium* in any step from coculture to regeneration.

2. The method according to claim 1, wherein 3) said method further does not comprise any step for culturing the immature cocultured embryo with a callus growth medium between the coculture step and the regeneration step.

3. The method according to claim 1 or 2, wherein the selection of transformed immature embryo based on the properties of a nucleic acid to be introduced by *Agrobacterium* is selection with a selective drug and a resistance gene for the selective drug.

4. The method according to claim 1, wherein the transformation enhancement in 1) is intended to improve the efficiency of introducing a gene of interest into maize or rice immature embryo, to improve the efficiency of inducing a callus from an immature embryo, or to improve the efficiency of regeneration from a transformed callus.

5. The method according to claim 1, wherein said method comprises addition of a compound belonging to benzoic herbicides in the coculture step.

6. The method according to claim 5, wherein the compound belonging to benzoic herbicides is of benzoic acid type, salicylic acid type or picolinic acid type.

7. The method according to claim 5 or 6, wherein the compound belonging to benzoic herbicides is 3,6-dichloro-o-anisic acid or 4-amino-3,5,6-trichloropicolinic acid.

* * * * *